United States Patent
Kaku et al.

(10) Patent No.: US 10,335,073 B2
(45) Date of Patent: Jul. 2, 2019

(54) ENDOSCOPE SYSTEM, PROCESSOR DEVICE THEREOF, AND METHOD FOR CONTROLLING ENDOSCOPE SYSTEM

(71) Applicant: FUJIFILM Corporation, Tokyo (JP)

(72) Inventors: Toshihiko Kaku, Ashigarakami-gun (JP); Jin Murayama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 735 days.

(21) Appl. No.: 13/934,419

(22) Filed: Jul. 3, 2013

(65) Prior Publication Data

US 2014/0012112 A1 Jan. 9, 2014

(30) Foreign Application Priority Data

Jul. 6, 2012 (JP) .................................. 2012-152642

(51) Int. Cl.
*A61B 5/00* (2006.01)
*A61B 5/1455* (2006.01)
(Continued)

(52) U.S. Cl.
CPC .......... *A61B 5/14552* (2013.01); *A61B 1/045* (2013.01); *A61B 1/051* (2013.01);
(Continued)

(58) Field of Classification Search
None
See application file for complete search history.

(56) References Cited

U.S. PATENT DOCUMENTS

| | | | |
|---|---|---|---|
| 5,233,416 A | * | 8/1993 | Inoue .............................. 348/70 |
| 5,512,940 A | * | 4/1996 | Takasugi et al. ............... 348/71 |

(Continued)

FOREIGN PATENT DOCUMENTS

| | | |
|---|---|---|
| EP | 2481340 A1 | 8/2012 |
| JP | 2011-110216 | 6/2011 |
| JP | 2012-016545 | 1/2012 |

OTHER PUBLICATIONS

Nasim Mansurov, "Understand ISO—A Beginner's Guide", Photography Life, <https://photographylife.com/what-is-iso-in-photography>, 2009.*

(Continued)

*Primary Examiner* — Tse W Chen
*Assistant Examiner* — Joanne M Hoffman
(74) *Attorney, Agent, or Firm* — Birch, Stewart, Kolasch & Birch, LLP

(57) ABSTRACT

An electronic endoscope has normal and high-sensitivity image sensors. In a special mode for imaging an oxygen saturation level of blood, one of the normal and high-sensitivity image sensors is selected in accordance with a reflected light amount of special illumination light. When the normal image sensor is selected, the normal image sensor captures an image under irradiation with the special illumination light and outputs a second normal-sensor image. When an average pixel value of the second normal-sensor image is less than a first sensor selection threshold value, the use of the high-sensitivity image sensor is started. When the high-sensitivity image sensor is selected, the high-sensitivity image sensor captures an image under irradiation with the special illumination light and outputs a high-sensitivity-sensor image. When the average pixel value of the high-sensitivity-sensor image is more than a second sensor selection threshold value, the use of the high-sensitivity image sensor is stopped.

11 Claims, 24 Drawing Sheets

(51) Int. Cl.
*A61B 1/045* (2006.01)
*A61B 1/05* (2006.01)
*A61B 1/06* (2006.01)
*A61B 1/04* (2006.01)
*A61B 1/00* (2006.01)

(52) U.S. Cl.
CPC ........ *A61B 1/0646* (2013.01); *A61B 1/00096* (2013.01); *A61B 1/043* (2013.01); *A61B 1/0638* (2013.01); *A61B 5/0084* (2013.01)

(56) References Cited

U.S. PATENT DOCUMENTS

| | | | |
|---|---|---|---|
| 6,097,025 A * | 8/2000 | Modlin et al. | 250/227.22 |
| 6,624,890 B2 * | 9/2003 | Backman | A61B 5/0084 356/369 |
| 6,642,955 B1 * | 11/2003 | Midgley et al. | 348/164 |
| 2003/0067530 A1 * | 4/2003 | Ishikawa | G02B 26/127 347/235 |
| 2005/0105077 A1 * | 5/2005 | Padmanabhan et al. | 356/39 |
| 2010/0245551 A1 | 9/2010 | Morita | |
| 2011/0158914 A1 * | 6/2011 | Yamada | 424/9.6 |

OTHER PUBLICATIONS

Kemney et al., "Multiresolution Image Sensor", IEEE Transactions on Circuits and Systems for Video Technology, vol. 7, No. 4, 1997.*
Japanese Office Action, dated Jun. 4, 2014, in application No. JP2012-152642.
European Office Communication, dated Aug. 24, 2015, for European Application No. 13 175 343.6.

* cited by examiner

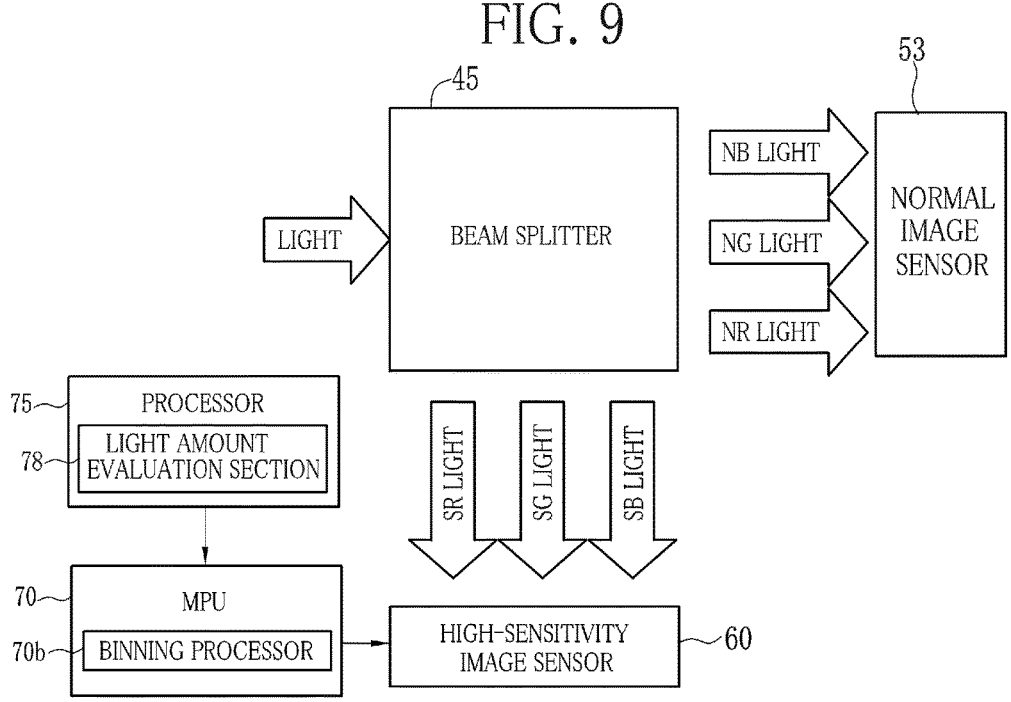
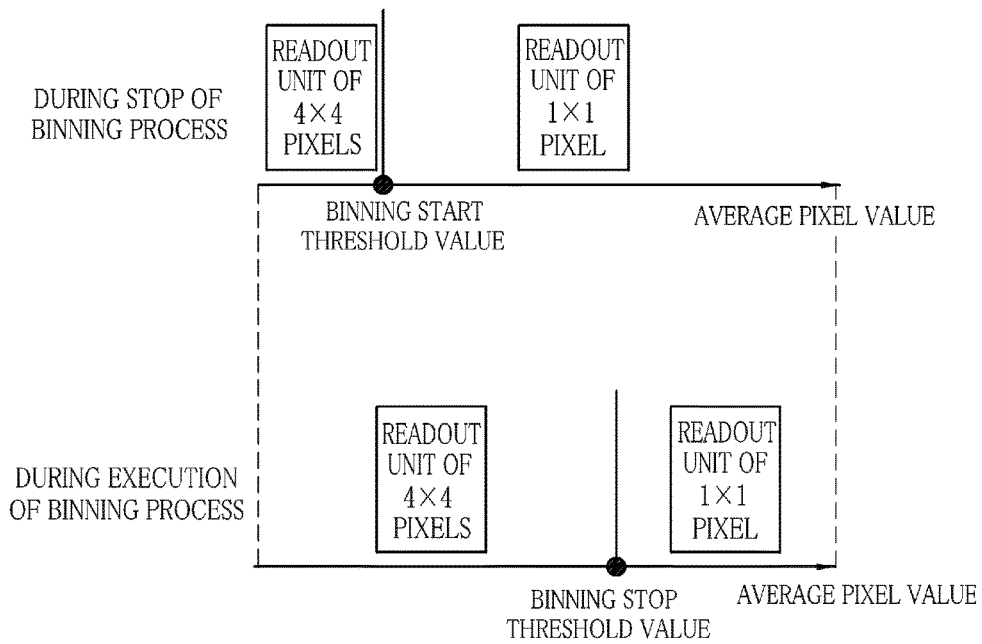

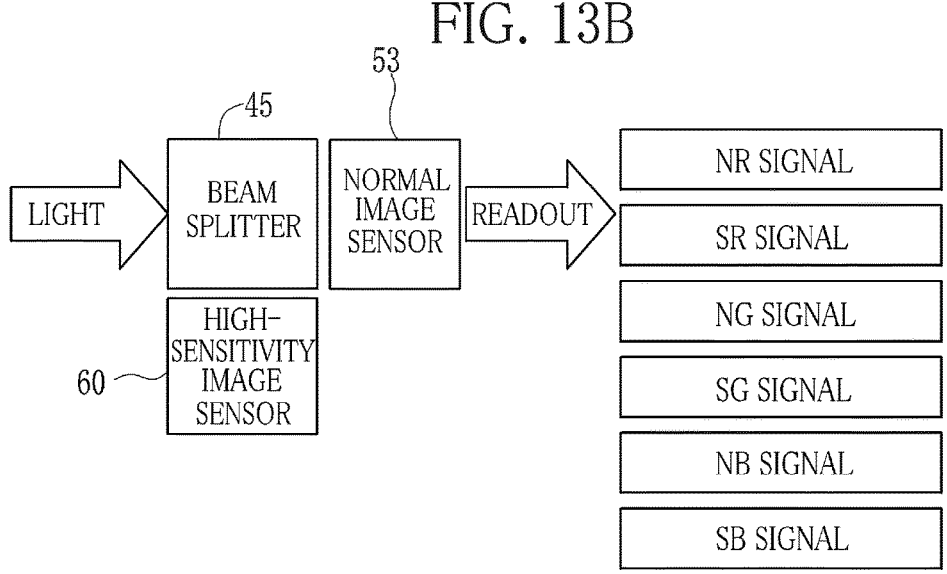

FIG. 14A

| LIGHT | NR | SHADING | SR | SHADING | NG | SHADING | SG | SHADING | NB | SHADING | SB | SHADING |
|---|---|---|---|---|---|---|---|---|---|---|---|---|
| NORMAL IMAGE SENSOR | IMAGING | READOUT | | RESET | IMAGING | READOUT | | RESET | IMAGING | READOUT | | RESET |
| HIGH-SENSITIVITY IMAGE SENSOR | | | IMAGING | READOUT | | RESET | IMAGING | READOUT | | RESET | IMAGING | READOUT |

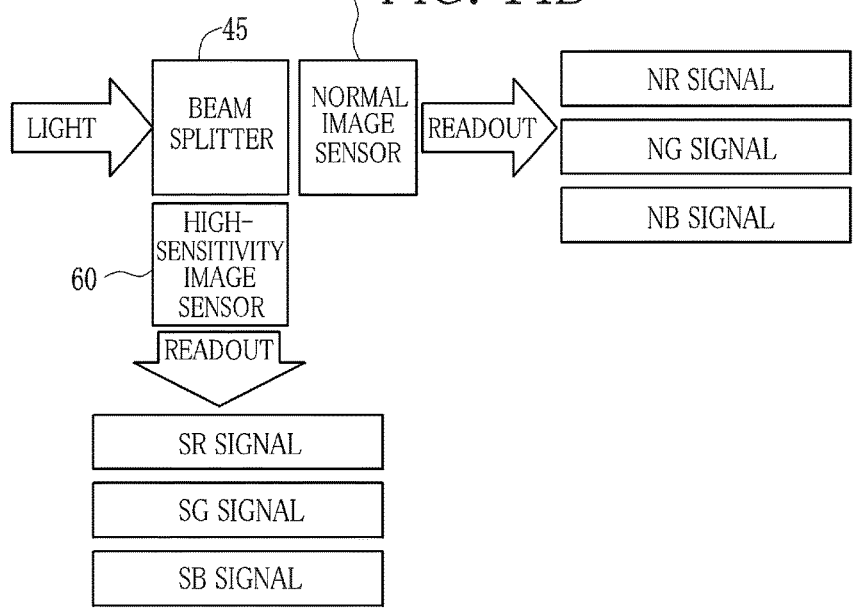

| LIGHT | NR | SR | NG | SG | NB | SB |
|---|---|---|---|---|---|---|
| NORMAL IMAGE SENSOR | IMAGING | READOUT | IMAGING | READOUT | IMAGING | READOUT |
| HIGH-SENSITIVITY IMAGE SENSOR | | IMAGING | READOUT | IMAGING | READOUT | IMAGING | READOUT |

| LIGHT | NR | SHADING | NG | SHADING | NB | SHADING | SB | | | SHADING |
|---|---|---|---|---|---|---|---|---|---|---|
| NORMAL IMAGE SENSOR | IMAGING | | IMAGING | | IMAGING | | IMAGING | | | |
| | | READOUT | | READOUT | | READOUT | | | | READOUT |
| HIGH-SENSITIVITY IMAGE SENSOR | | | | | | | | | | |
| | | | | | | | | | | |

| LIGHT | NR | SHADING | NG | SHADING | NB | SHADING | SB | | | SHADING |
|---|---|---|---|---|---|---|---|---|---|---|
| NORMAL IMAGE SENSOR | IMAGING | | IMAGING | | IMAGING | | | | | |
| | | READOUT | | READOUT | | READOUT | | | | RESET |
| HIGH-SENSITIVITY IMAGE SENSOR | | | | | | | IMAGING | | | |
| | | | | | | RESET | | | | READOUT |

FIG. 28C

| LIGHT | NR | NG | NB | SB | | |
|---|---|---|---|---|---|---|
| NORMAL IMAGE SENSOR | IMAGING | IMAGING | IMAGING | IMAGING | | |
| | | READOUT | READOUT | READOUT | | READOUT |
| HIGH-SENSITIVITY IMAGE SENSOR | | | | | | |

FIG. 28D

| LIGHT | NR | NG | NB | SB | | |
|---|---|---|---|---|---|---|
| NORMAL IMAGE SENSOR | IMAGING | IMAGING | IMAGING | | | |
| | | READOUT | READOUT | READOUT | | |
| HIGH-SENSITIVITY IMAGE SENSOR | | | | IMAGING | | |
| | | | | | | READOUT |

| LIGHT | NORMAL LIGHT | | SPECIAL LIGHT | |
|---|---|---|---|---|
| NORMAL IMAGE SENSOR | IMAGING | READOUT | IMAGING | READOUT |
| HIGH-SENSITIVITY IMAGE SENSOR | | | | |

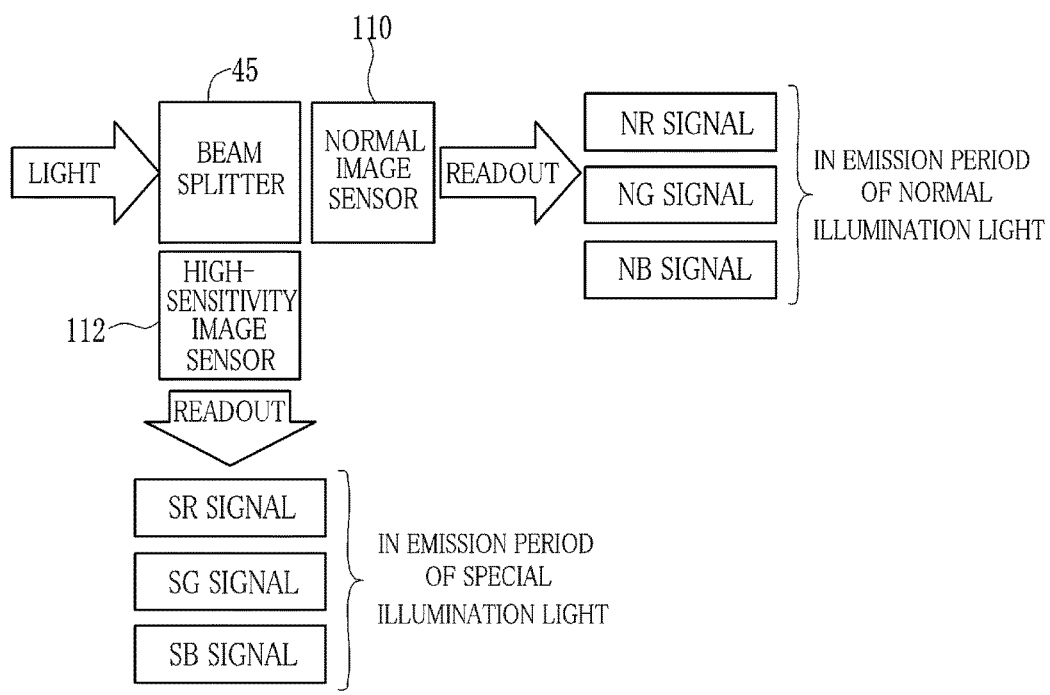

ENDOSCOPE SYSTEM, PROCESSOR DEVICE THEREOF, AND METHOD FOR CONTROLLING ENDOSCOPE SYSTEM

BACKGROUND OF THE INVENTION

1. Field of the Invention

The present invention relates to an endoscope system that obtains information about blood such as an oxygen saturation level of blood, a processor device of the endoscope system, and a method for controlling the endoscope system.

2. Description Related to the Prior Art

In a medical field, an endoscope system is used often for diagnosis and treatment. The endoscope system is constituted of an electronic endoscope to be inserted into a human body cavity, a light source device for supplying illumination light to the electronic endoscope, and a processor device that processes an image signal produced by the electronic endoscope and displays a processed image on a monitor. There is known an endoscope system that carries out not only normal observation for imaging an internal body portion under irradiation with white light (normal light), but also special observation for imaging the internal body portion under irradiation with specific narrow band light (special light).

As the special observation, an oxygen saturation level obtaining technique is known using first light being narrow band light having a wavelength range in which an absorption coefficient is different between oxyhemoglobin and deoxyhemoglobin, and second light having a wavelength range different from that of the first light. The first and second light is applied sequentially to the internal body portion in order to determine an oxygen saturation level of blood. The determined oxygen saturation level is reflected in a normal image obtained in the normal observation, to produce a special image in which a hypoxic region being a cancer-suspected lesion is colored artificially.

The normal image mainly aims to look at details of mucosal structure, including blood vessels, projections and depressions, and the like. Thus, the normal image requires high resolution. In the special image, on the other hand, the hypoxic region extends a certain size, so the high resolution is not required. However, the special image requires high sensitivity to reflected light, because the oxygen saturation level is calculated from the light amount of the first and second light reflected from the internal body portion. For this reason, high-intensity narrow band light emitted from an LD, LED, or light source rivaling the LD or LED is needed as the first and second light. In the case of not using the high-intensity narrow band light, a high-sensitivity image sensor becomes necessary.

Accordingly, US Patent Application Publication No. 2010/0245551 discloses an endoscope system that is provided with two image sensors i.e. a normal image sensor having normal sensitivity and a high-sensitivity image sensor having high sensitivity. In this system, the normal image sensor is used in the normal observation requiring high resolution, while the high-sensitivity image sensor is used in the special observation requiring high sensitivity.

In the US Patent Application Publication No. 2010/0245551, the high-sensitivity image sensor is used for detecting weak autofluorescence distributed through a wide wavelength range. On the other hand, the first and second light used for calculation of the oxygen saturation level has the specific wavelength ranges, so the light amount of the first and second light is not as low as that of the autofluorescence, though is lower than that of the white light. Therefore, in a short-distance view in which a distal end portion of the electronic endoscope is near the body portion, even the normal sensor can detect an enough light amount to calculate the oxygen saturation level. When the normal sensor is adequate, it is desirable to use the normal image sensor having high resolution, instead of the high-sensitivity image sensor.

SUMMARY OF THE INVENTION

An object of the present invention is to provide an endoscope system that can produce a special image having as high resolution as possible, while securing sensitivity required for calculating an oxygen saturation level of blood, a processor device of the endoscope system, and a method for controlling the endoscope system.

To achieve the above and other objects, an endoscope system according to the present invention includes a lighting section, an imaging section, a light amount measurement section, an imaging control section, and a special image processing section. The lighting section applies special illumination light to a body portion. The special illumination light has a wavelength at which oxyhemoglobin and deoxyhemoglobin have different absorption coefficients. The imaging section has a normal image sensor and a high-sensitivity image sensor. The imaging section captures an image of the body portion irradiated with the special illumination light. The light amount measurement section measures a reflected light amount of the special illumination light based on a signal obtained by the imaging section. The imaging control section changes operating conditions of the normal and high-sensitivity image sensors in accordance with the reflected light amount. The special image processing section produces a special image depicting an oxygen saturation level of blood based on the signal obtained by the imaging section under control of the imaging control section.

The imaging control section preferably chooses which one of the normal and high-sensitivity image sensors to use for imaging the body portion irradiated with the special illumination light in accordance with the reflected light amount of the special illumination light. The special image processing section preferably produces the special image based on a signal obtained by selected one of the normal and high-sensitivity image sensors.

The light amount measurement section preferably measures the reflected light amount of the special illumination light repeatedly in certain cycles. The imaging control section preferably chooses which one of the normal and high-sensitivity image sensors to use based on the reflected light amount. When the normal image sensor is used, the imaging control section preferably stops using the normal image sensor and starts using the high-sensitivity image sensor, if the reflected light amount is less than a first sensor selection threshold value. When the high-sensitivity image sensor is used, the imaging control section preferably stops using the high-sensitivity image sensor and starts using the normal image sensor, if the reflected light amount is more than a second sensor selection threshold value. The second sensor selection threshold value is preferably larger than the first sensor selection threshold value.

The lighting section may sequentially apply to the body portion the special illumination light and normal illumination light having a broad wavelength band. The normal illumination light is used for producing a normal image.

When the reflected light amount of the special illumination light is low, the imaging control section preferably controls the normal and high-sensitivity image sensors such that the normal image sensor captures the image under irradiation with the normal illumination light, and the high-sensitivity image sensor captures the image under irradiation with the special illumination light. When the reflected light amount of the special illumination light is not low, the imaging control section preferably controls the normal and high-sensitivity image sensors such that the normal image sensor captures the image under irradiation with the normal illumination light and the special illumination light.

The normal illumination light may include red light, green light, and blue light. The special illumination light may include at least blue narrow band light having a wavelength at which oxyhemoglobin and deoxyhemoglobin have different absorption coefficients. The lighting section may selectively emit the red light, the green light, the blue light, and the blue narrow band light.

The normal illumination light may be first emission light including first blue narrow band light and fluorescence obtained by wavelength conversion of the first blue narrow band light by a wavelength conversion element. The special illumination light may be second emission light including second blue narrow band light and fluorescence obtained by wavelength conversion of the second blue narrow band light by the wavelength conversion element. The lighting section may selectively emit the first and second emission light.

The sensitivity of the high-sensitivity image sensor is preferably 2 to 200 times that of the normal image sensor.

When the reflected light amount of the special illumination light is low, the normal image sensor preferably captures the image under irradiation with the normal illumination light and outputs a color normal signal, and the high-sensitivity image sensor preferably captures the image under irradiation with the special illumination light and outputs a special signal. The special image processing section preferably produces the special image based on the special signal and a specific color signal of the color normal signal.

When the reflected light amount of the special illumination light is not low, the normal image sensor preferably captures the image under irradiation with the normal illumination light and outputs the color normal signal, and captures the image under irradiation with the special illumination light and outputs the special signal. The special image processing section preferably produces the special image based on the special signal and the specific color signal of the color normal signal.

The endoscope system may further include a beam splitter for splitting the special illumination light reflected from the body portion into two beams. One of the two beams is incident upon the normal image sensor. The other of the two beams is incident upon the high-sensitivity image sensor. When a first optical path between the beam splitter and the normal image sensor is not equivalent with a second optical path between the beam splitter and the high-sensitivity image sensor, an effective area is preferably defined in each of the normal and high-sensitivity image sensors in such a position as to correspond to an overlapping area in which object images obtained by the normal and high-sensitivity image sensors overlap each other.

A processor device of an endoscope system includes a light amount measurement section, an imaging control section, and a special image processing section. The light amount measurement section measures a reflected light amount of the special illumination light based on a signal obtained by the imaging section. The imaging control section changes operating conditions of the normal and high-sensitivity image sensors in accordance with the reflected light amount. The special image processing section produces a special image depicting an oxygen saturation level of blood based on the signal obtained by the imaging section under control of the imaging control section.

A method for controlling an endoscope system includes the steps of applying special illumination light to a body portion; guiding the special illumination light reflected from the body portion to an imaging section; measuring a reflected light amount of the special illumination light based on a signal obtained by the imaging section; changing operating conditions of the normal and high-sensitivity image sensors in accordance with the measured reflected light amount; operating the normal and high-sensitivity image sensors in the changed operating conditions, and imaging the body portion under irradiation with the special illumination light; and producing a special image depicting an oxygen saturation level of blood based on an image signal obtained by the normal or high-sensitivity image sensor.

According to the present invention, the operating conditions of the normal and high-sensitivity image sensors are changed in accordance with the reflected light amount of the special illumination light. For example, when the reflected light amount is low, the high-sensitivity image sensor is used to obtain a signal having adequate intensity for calculating the oxygen saturation level. When the reflected light amount is not low, on the other hand, the normal image sensor is used to obtain a high resolution image. Therefore, it is possible to produce the special image having as high resolution as possible, while securing sensitivity required for calculating the oxygen saturation level.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 9 is an explanatory view of a binning process in the first embodiment;

FIG. 10 is an explanatory view of the relation between a binning start threshold value and a binning stop threshold value;

FIG. 13A is a timing chart showing imaging and readout timing in a case where the light amount of reflected special light is not judged to be low in the first embodiment;

FIG. 13B is an explanatory view of output of normal signals and special signals in a case where the light amount is not judged to be low;

FIG. 13C is a timing chart in the case of using a FIT or IT type monochrome normal image sensor;

FIG. 14A is a timing chart showing imaging and readout timing in a case where the light amount of the reflected special light is judged to be low in the first embodiment;

FIG. 14B is an explanatory view of output of the normal signals and the special signals in a case where the light amount is judged to be low;

FIG. 14C is a timing chart in the case of using a FIT or IT type monochrome high-sensitivity image sensor;

FIG. 28C is a timing chart showing imaging timing of the FIT or IT type monochrome normal image sensor in which an emission period of SB light is elongated;

FIG. 28D is a timing chart showing the imaging timing of the FIT or IT type monochrome normal and high-sensitivity image sensors in which the emission period of the SB light is elongated;

FIG. 35A is a timing chart showing the imaging and readout timing in a case where the light amount of the reflected special light is, judged to be low in the fourth embodiment;

FIG. 35B is an explanatory view of output of the normal signals and the special signals in a case where the light amount is judged to be low;

DESCRIPTION OF THE PREFERRED EMBODIMENTS

First Embodiment

Figure 1:
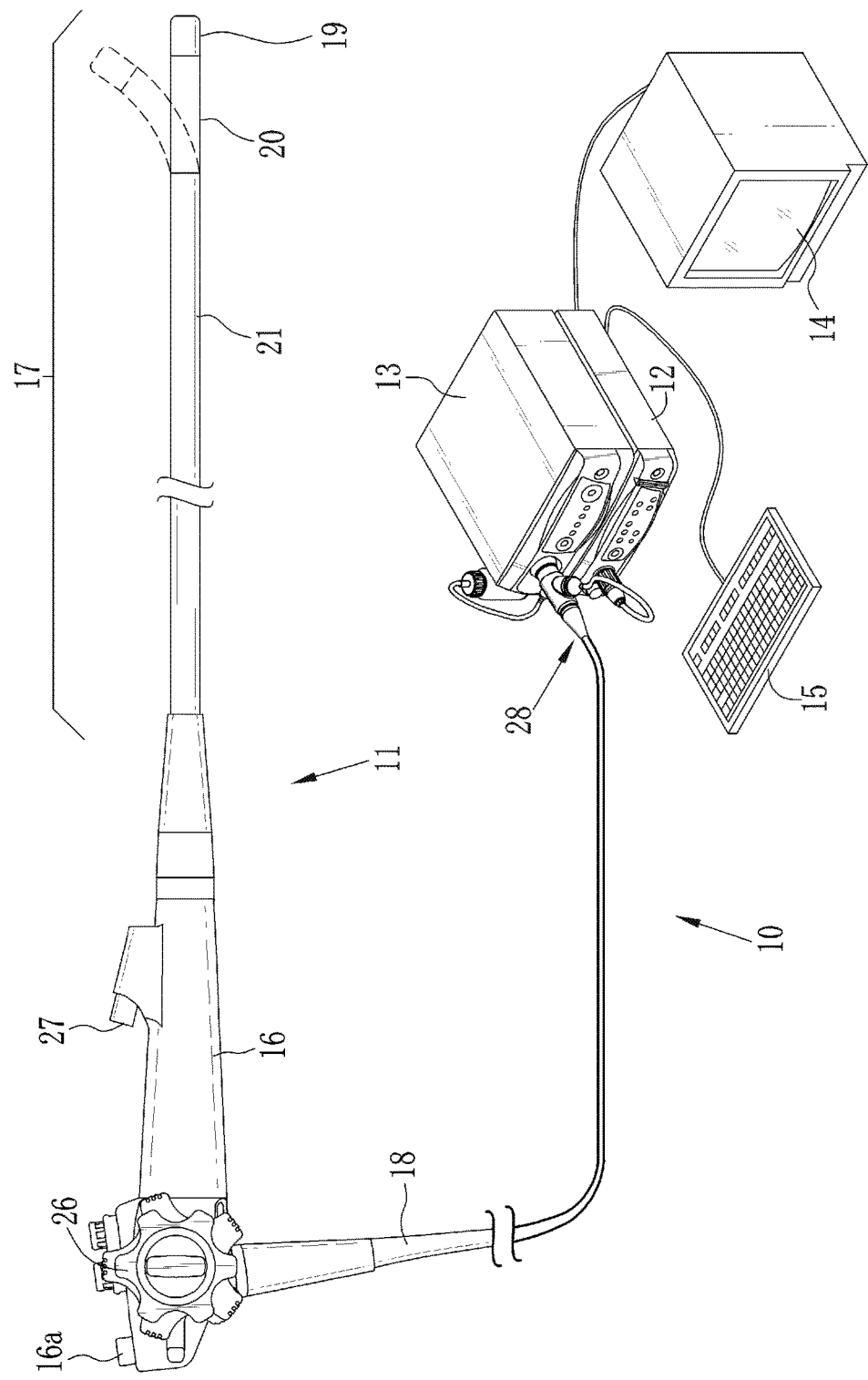
FIG. 1 is a perspective view of an endoscope system.

As shown in FIG. 1, an endoscope system 10 according to a first embodiment is constituted of an electronic endoscope 11, a processor device 12, a light source device 13, a monitor 14, and an input device 15 including a keyboard, a mouse, and the like. The electronic endoscope 11 images an internal body portion. The processor device 12 applies image processing to an image signal obtained by the electronic endoscope 11. The light source device 13 supplies illumination light to the internal body portion. A produced image is displayed on the monitor 14.

The endoscope system 10 has a normal mode to grasp an overview of the internal body portion and a special mode to observe an oxygen saturation level of blood flowing through a blood vessel in the body portion. The endoscope system 10 is switched between the normal mode and the special mode by operating the input device 15 or a mode switch 16a provided on a control handle unit 16 of the electronic endoscope 11. The input device 15 and the mode switch 16a are connected to an MPU 70 (see FIG. 2) of the processor device 12.

The electronic endoscope 11 includes a flexible insert section 17 to be introduced into a human body, the control handle unit 16 provided at a proximal end of the insert section 17, and a universal cord 18 for connecting the control handle unit 16 to the processor device 12 and the light source device 13.

Figure 2:
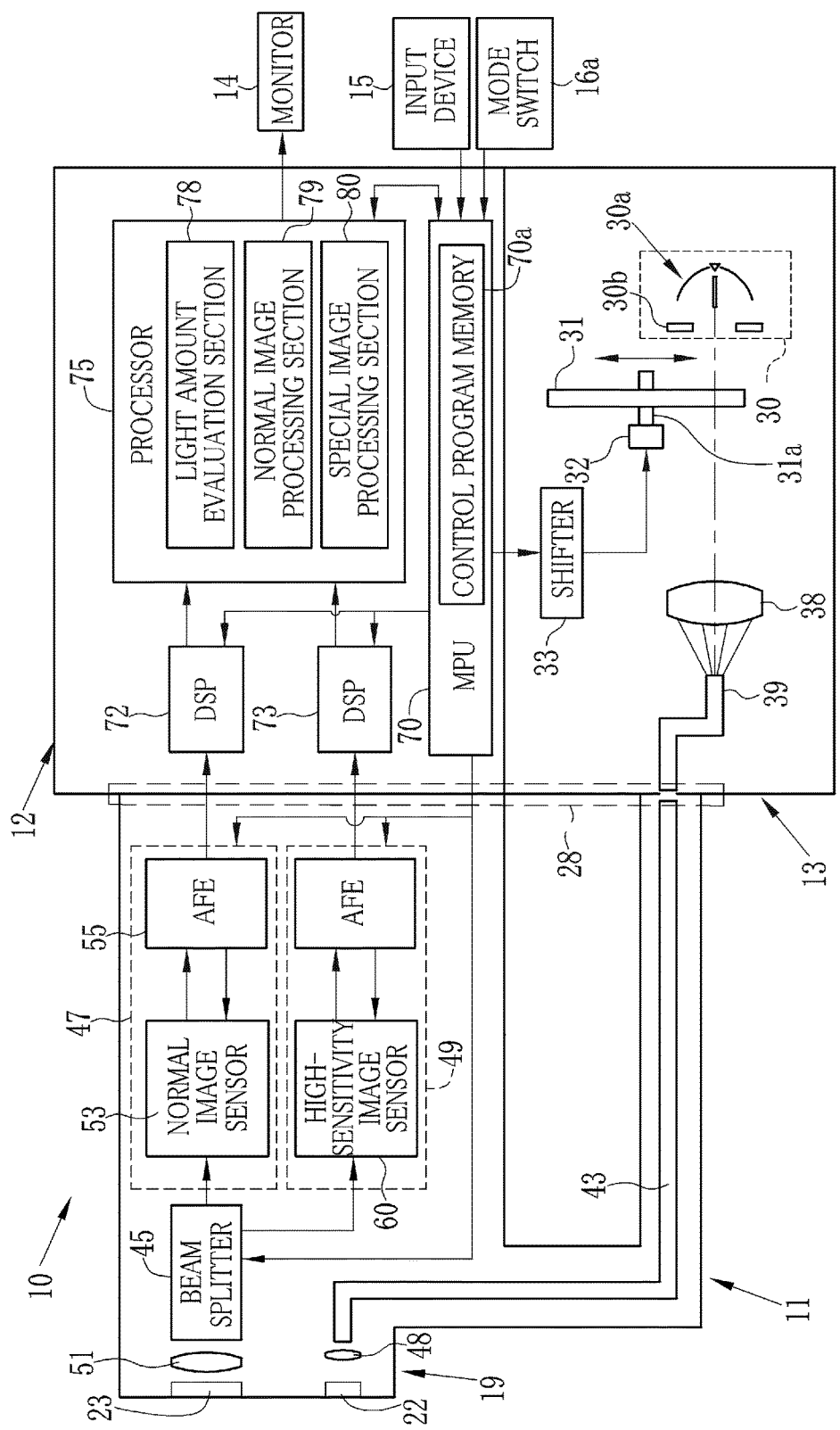
FIG. 2 is a block diagram of the endoscope system according to a first embodiment.

The insert section 17 includes a head assembly 19, a steering assembly 20, and a flexible elongated tube 21 disposed in this order from a distal end to the proximal end of the insert section 17. As shown in FIG. 2, a distal end surface of the head assembly 19 is provided with lighting windows 22, an imaging window 23, air/water feeding nozzles (not shown), and a forceps outlet port (not shown). The illumination light is applied to the internal body portion through the lighting windows 22. The imaging window. 23 allows the light reflected from the body portion to pass through. The air/water feeding nozzles feed air and water to clean the imaging window 23. From the forceps outlet port, a medical instrument such as a forceps and an electric knife is projected. Behind the imaging window 23, there are provided an image forming optical system, a normal imaging unit 47, a high-sensitivity imaging unit 49, and the like.

The steering assembly 20 is composed of a train of joint pieces. The steering assembly 20 is bent flexibly in an arbitrary direction in response to operation of an angle knob 26 provided on the control handle unit 16. The bend of the steering assembly 20 aims the head assembly 19 at a desired direction. The elongated tube 21 is flexible so as to be inserted into a serpentine canal such as esophagus and intestine. Through the insert section 17, a communication cable and a light guide 43 (see FIG. 2) are disposed. The communication cable is used for establishing communication with the normal imaging unit 47 and the high-sensitivity imaging unit 49. The light guide 43 leads the illumination light from the light source device 13 to the lighting windows 22.

The control handle unit 16 is provided with the angle knob 26, a forceps inlet port 27 through which the medical instrument is inserted, an air/water feeding button triggering airing and watering operation, a release button to be pressed in taking an static image, and the like.

The communication cable and the light guide 43, which extend from the insert section 17, are disposed through the universal cord 18. The universal cord 18 has at its distal end a multi connector 28 having a communication connector and a light source connector. The communication connector contains an end of the communication cable. The light source connector contains an end of the light guide 43. The electronic endoscope 11 is detachably connected to the processor device 12 and the light source device 13 via the multi connector 28.

The light source device 13 is provided with a white light source unit 30, a rotary filter 31, a motor 32, and a shifter 33. The white light source unit 30 has a light source 30a and an aperture stop 30b. The light source 30a, being composed of a xenon lamp, a halogen lamp, a metal halide lamp, or the like, emits broad band light BB (see FIG. 4) having a wavelength band of 400 to 700 nm. The aperture stop 30b is driven by the MPU 70 of the processor device 12 to control the light amount of the broad band light BB.

Figure 3:
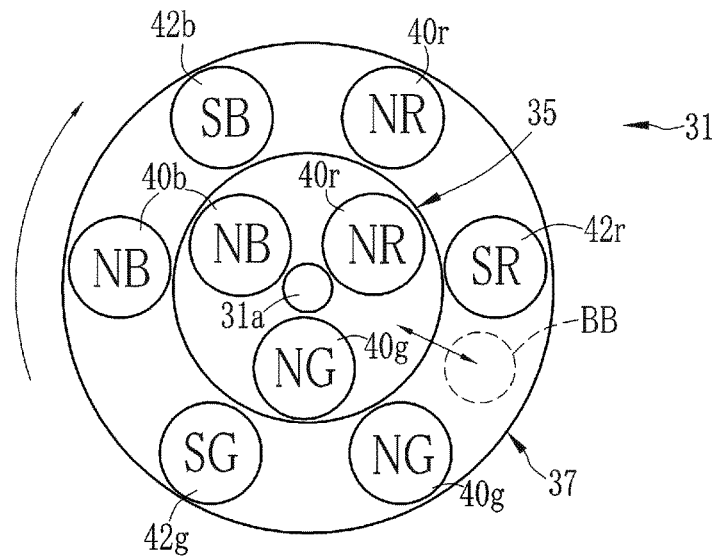
FIG. 3 is a top plan view of a rotary filter according to the first embodiment.

The motor 32 rotates the rotary filter 31 about a rotary shaft 31a. As shown in FIG. 3, the rotary filter 31 is provided with an inner radial portion 35 that is near the rotary shaft 31a and an outer radial portion 37 that is far from the rotary shaft 31a. The shifter 33 shifts the rotary filter 31 in a radial direction. Thus, in the normal mode, the rotary filter 31 is shifted to an inner position in which the inner radial portion 35 is disposed in an optical path of the broad band light BB. In the special mode, the rotary filter 31 is shifted to an outer position in which the outer radial portion 37 is disposed in the optical path of the broad band light BB.

In the inner radial portion 35, an NR filter 40r, an NG filter 40g, an NB filter 40b are formed in its circumferential direction. A light shielding portion is formed between the NR filter 40r and the NG filter 40g, between the NG filter 40g and the NB filter 40b, and between the NB filter 40b and the NR filter 40r to block the broad band light BB. The outer radial portion 37 is provided with six filters, i.e. an NR filter 40r, an SR filter 42r, an NG filter 40g, an SG filter 42g, an NB filter 40b, and an SB filter 42b disposed in its circumferential direction. A light shielding portion is formed between two of the filters 40r, 42r, 40g, 42g, 40b, and 42b adjoining each other to block the broad band light BB.

Figure 4:
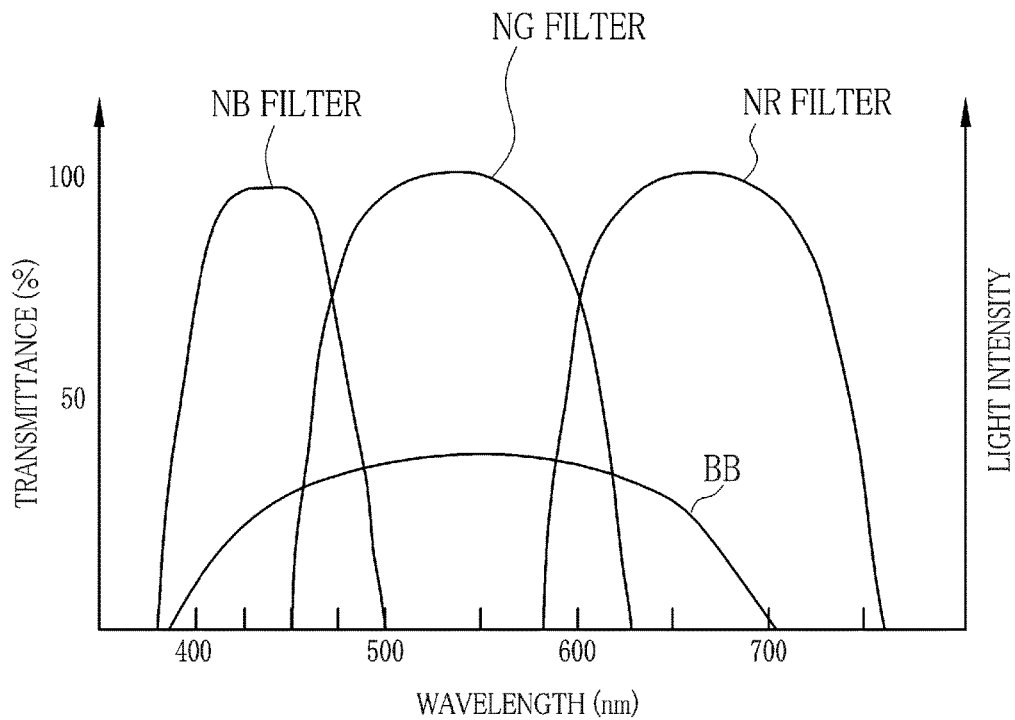
FIG. 4 is a graph showing transmission spectra of NB, NG, and NR filters and emission spectrum of broad band light BB.

As shown in FIG. 4, the NR filter 40r, the NG filter 40g, and the NB filter 40b transmit red band light, green band light, and blue band light, which are required for producing a normal image, respectively, out of the broad band light BB. The NR filter 40r transmits normal red light (NR light) having a wavelength band of 580 to 760 nm out of the broad band light BB. The NG filter 40g transmits normal green light (NG light) having a wavelength band of 450 to 630 nm. The NB filter 40b transmits normal blue light (NB light) having a wavelength band of 380 to 500 nm.

The SR filter 42r, the SG filter 42g, and the SB filter 42b transmit red band light, green band light, and blue band light, which are required for calculating the oxygen saturation level, respectively, out of the broad band light BB. The SR filter 42r transmits special red light (SR light) in a wavelength hand of 600 to 700 nm. The SG filter 42g transmits special green light (SG light) in a wavelength band of 500 to 590 nm. The SB filter 42b transmits special blue light (SB light) in a narrow wavelength band of 473±10 nm.

Figure 5A:
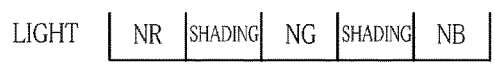
FIG. 5A is an explanatory view of an emission pattern in a normal mode according to the first embodiment.

In the normal mode, as shown in FIG. 5A, by the rotation of the rotary filter 31 set in the inner position, the NR, NG, and NB light is applied in this order to the internal body portion. There is provided a certain light shielding period between individual applications of the light. The NR, NG, and NB light enters the light guide 43 through a condenser lens 38 and a rod integrator 39.

Figure 5B:
FIG. 5B is an explanatory view of an emission pattern in a special mode according to the first embodiment.

In the special mode, as shown in FIG. 5B, by the rotation of the rotary filter 31 set in the outer position, the NR, SR, NG, SG, NB, and SB light is applied in this order to the internal body portion. There is provided a certain light shielding period between individual applications of the light. The NR, SR, NG, SG, NB, and SB light enters the light guide 43 through the condenser lens 38 and the rod integrator 39.

Figure 6:
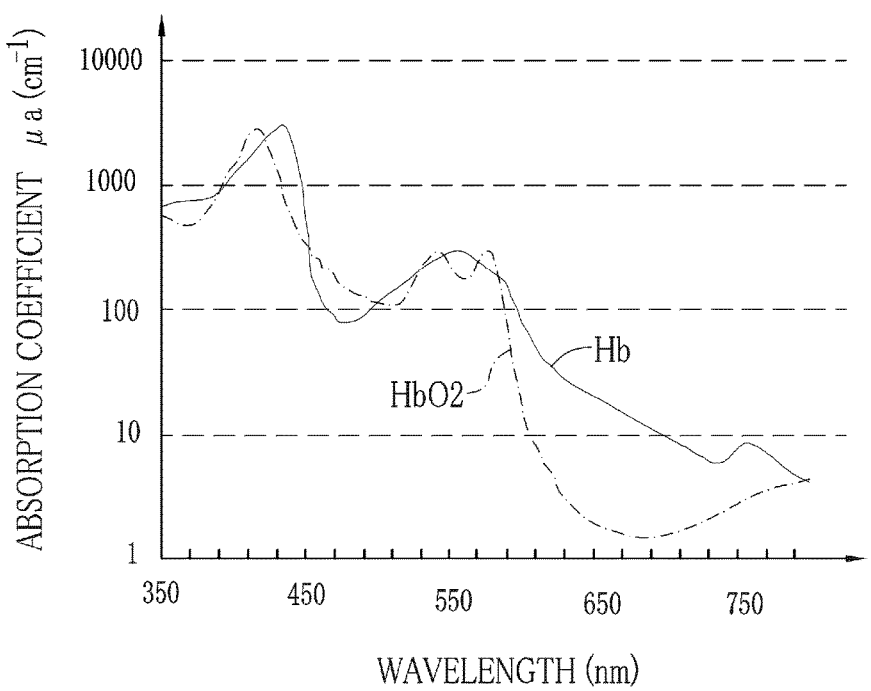
FIG. 6 is a graph of an absorption coefficient of oxyhemoglobin and deoxyhemoglobin.

As shown in FIG. 6, in a wavelength band of 473±10 nm of the SB light, oxyhemoglobin (HbO2) has a higher absorption coefficient than deoxyhemoglobin (Hb). For this reason, when the SB light is applied to the blood vessel, the intensity of the reflected SB light decreases with increase in the oxygen saturation level of blood. In other words, the higher the oxygen saturation level, the darker the blood vessel is seen. Note that, the transmission wavelength bands of the SR filter 42r and the SG filter 42g may be narrowed, as with that of the SB filter 42b. Also in this case, the oxyhemoglobin (HbO2) has a higher absorption coefficient than the deoxyhemoglobin (Hb) in the transmission wavelength bands of the SR filter 42r and the SG filter 42g.

As shown in FIG. 2, the electronic endoscope 11 is provided with the light guide 43, a beam splitter 45, a normal imaging unit 47, and a high-sensitivity imaging unit 49. The light guide 43 is made of a large-diameter optical fiber, a fiber bundle, or the like. By the connection of the multi connector 28 to the light source device 13, a light incident end of the light guide 43 is opposed to a light exit end of the rod integrator 39 of the light source device 13.

Figure 7:
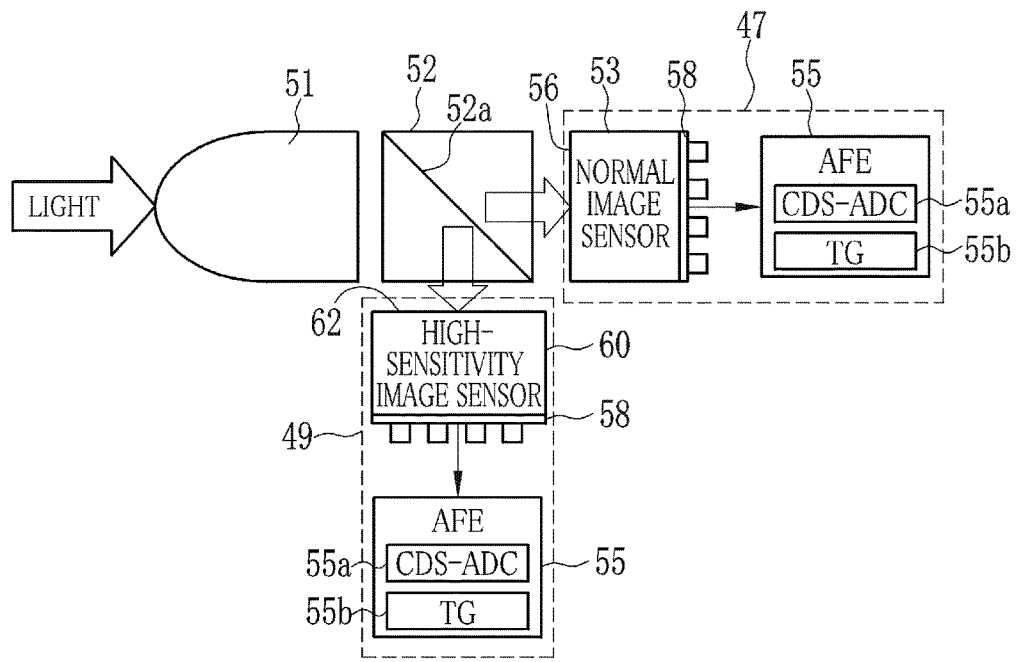
FIG. 7 is a block diagram of an imaging section.

A lighting lens 48 for regulating a light distribution angle of the illumination light is disposed in front of each lighting window 22. The illumination light transmitted through the light guide 43 is applied to the internal body portion through the lighting windows 22. The light reflected from the body portion is incident upon an image-forming lens 51 through the imaging window 23. The light exits from the image-forming lens 51, and is separated into two beams by the beam splitter 45. The beam splitter 45 is composed of a prism 52, as shown in FIG. 7. The prism 52 has a beam splitting surface 52a to split the incident light. One of the two beams split by the beam splitting surface 52a is incident upon a monochrome normal image sensor 53 of the normal imaging unit 47, while the other one is incident upon a monochrome high-sensitivity image sensor 60 of the high-sensitivity imaging unit 49. The image-forming lens 51, the prism 52, the normal imaging unit 47, and the high-sensitivity imaging unit 49 compose an imaging section.

The normal imaging unit 47 includes the monochrome normal image sensor 53 and an AFE 55. The MPU 70 controls the operation of the normal imaging unit 47. The normal image sensor 53 is a FT (frame transfer), FIT (frame interline transfer), or IT (interline transfer) type CCD image sensor having a frame rate of 30 or 60 f/s, for example. The normal image sensor 53 has a light receiving surface 56 upon which the light is incident from the prism 52. The light receiving surface 56 has a matrix of pixels. Each pixel, being made of a photoelectric conversion element such as a photodiode, performs photoelectric conversion of received light and accumulates signal charge by an amount corresponding to the amount of the received light. The signal charge is read out on a pixel-by-pixel basis, and transmitted to the AFE 55 as an image signal. Note that, the rotary filter 31 necessarily has the light shielding portions in the case of using the FT type CCD image sensor, as shown in FIG. 3, but may not have the light shielding portions in the case of using the FIT or IT type CCD image sensor.

Figure 8:
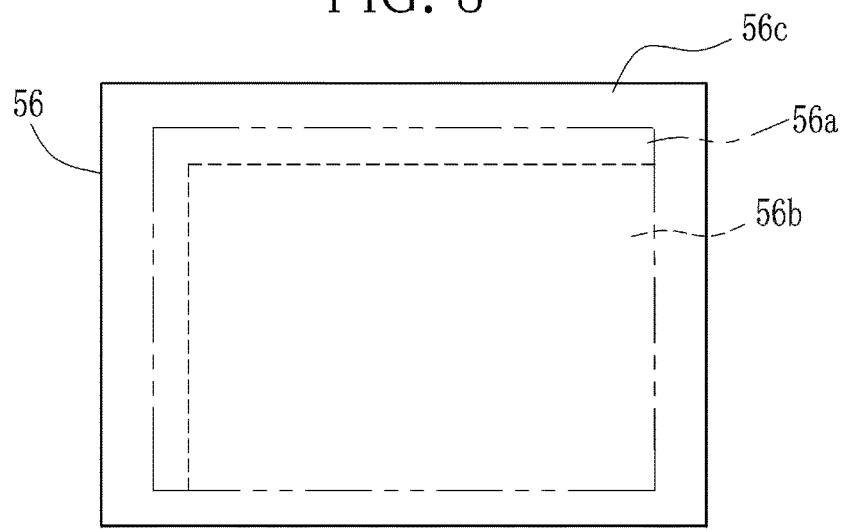
FIG. 8 is a top plan view of a light receiving surface of a monochrome normal image sensor.

A Peltier element 58 is provided on the normal image sensor 53 on a side opposite to the light receiving surface 56. The Peltier element 58 dissipates heat produced by the normal image sensor 53 to cool the normal image sensor 53. Cooling the normal image sensor 53 contributes to reduction in dark current, which occurs in a dark area 56c of the light receiving surface 56. The dark area 56c is an area that receives no reflected light, as shown in FIG. 8. Thus, the ratio of output from a light receiving area 56a, which receives the reflected light, to the image signal is increased, and hence the sensitivity of the normal image sensor 53 is improved. For example, a reduction of 8° C. in temperature of the normal image sensor 53 doubles the sensitivity. Note that, the Peltier element 58 is not necessarily provided on the normal image sensor 53.

The AFE 55 includes a CDS-ADC 55a having a correlated double sampling circuit and an analog-to-digital converter, and a TG (timing generator) 55b. The CDS-ADC 55a applies correlated double sampling processing to the image signal outputted from the normal image sensor 53, to remove noise from the image signal. After the noise removal, the image signal is converted into a digital image signal of a predetermined bit number, and inputted to a DSP 72 of the processor device 13. The TG 55b generates a drive signal to control drive of the normal image sensor 53 such as imaging timing.

Figure 11:
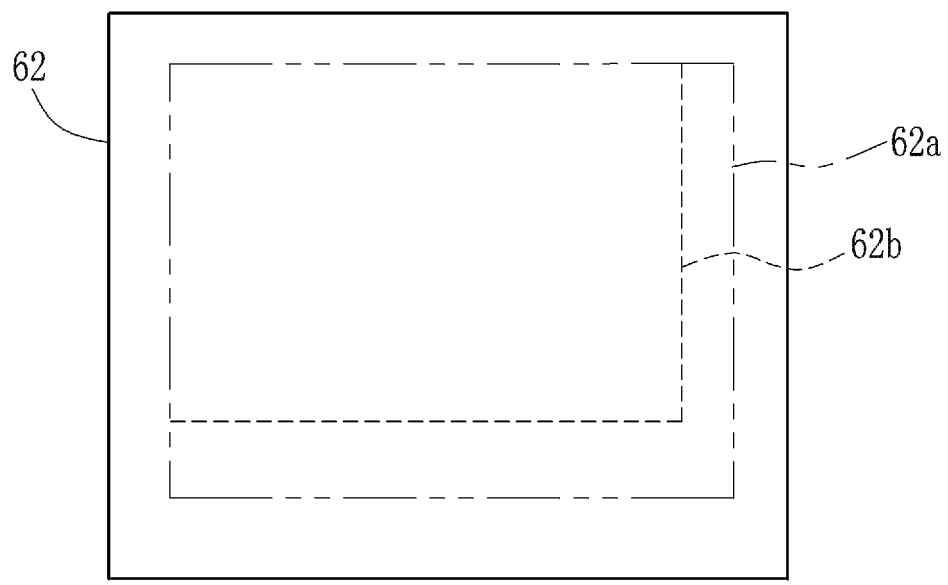
FIG. 11 is a top plan view of a light receiving surface of a monochrome high-sensitivity image sensor.

The high-sensitivity imaging unit 49 has a monochrome high-sensitivity image sensor 60 and an AFE 55, and is driven by the MPU 70 as with the normal imaging unit 47. The MPU 70 functions as an imaging control section, which changes operating conditions of the normal imaging unit 47 and the high-sensitivity imaging unit 49. As shown in FIG. 11, the high-sensitivity image sensor 60 has a light receiving surface 62 upon which the light is incident from the prism 52. The light receiving surface 62 has a matrix of pixels. As with the normal image sensor 53, the high-sensitivity image sensor 60 performs photoelectric conversion of received light at its light receiving surface 62, and reads out an image signal obtained thereby. The read image signal is transmitted to the AFE 55. The AFE 55 of the high-sensitivity imaging unit 49 has the same function as that of the AFE 55 of the normal imaging unit 47. The image signal after being processed by the AFE 55 is inputted to a DSP 73 of the processor device 13.

The pixel of the high-sensitivity image sensor 60 is composed of an avalanche photodiode, for example. Thus, the high-sensitivity image sensor 60 has higher sensitivity than the normal image sensor 53 owing to an avalanche multiplication effect. For example, the sensitivity of the high-sensitivity image sensor 60 is 2 to 200 times as much as that of the normal image sensor 53. In other words, the sensitivity ratio between the normal image sensor 53 and the high-sensitivity image sensor 60 is on the order of 1:200 at the maximum.

The high-sensitivity image sensor 60 needs cooling to take full advantage of the avalanche multiplication effect. Thus, a Peltier element 58 is provided on the high-sensitivity image sensor 60 on a side opposite to the light receiving surface 62. The Peltier element 58 dissipates heat produced by the high-sensitivity image sensor 60 to cool the high-sensitivity image sensor 60. The high-sensitivity image sensor 60 that is cooled to 40° C. using the Peltier element 58 has sensitivity approximately 32 times as much as the high-sensitivity image sensor 60 without being cooled.

As with the normal image sensor 53, the high-sensitivity image sensor 60 is an FT, FIT, or IT type CCD image sensor. This high-sensitivity image sensor 60 operates at a frame rate lower than that of the normal image sensor 53. For example, when the normal image sensor 53 has a frame rate of 30 f/s, the high-sensitivity image sensor 60 may have a frame rate of 15 f/s or 7.5 f/s. Reducing the frame rate allows to elongate charge accumulation time, and hence increase the amount of light taken in the high-sensitivity image sensor 60. In addition to elongating the charge accumulation time, cooling the high-sensitivity image sensor 60 using the Peltier element 58 or the like can improve an S/N ratio. The high-sensitivity image sensor 60 has a total pixel number of "$1/n^2$" and sensitivity of "$n^2$", with respect to the normal image sensor 53.

The normal image sensor 53 and the high-sensitivity image sensor 60 may have the same or different pixel number. The pixels of the normal image sensor 53 and the high-sensitivity image sensor 60 may be rectangular or in another form. The normal image sensor 53 and the high-sensitivity image sensor 60 have the same or different aspect ratio (length-to-width ratio).

The normal image sensor 53 and the high-sensitivity image sensor 60 have to be laid out such that an object image formed on the light receiving surface 56 of the normal image sensor 53 and an object image formed on the light receiving surface 62 of the high-sensitivity image sensor 60 become almost equal. Thus, it is preferable to approximately equalize an optical path of light exiting from the beam splitter 45 and entering the normal image sensor 53 with an optical path of light exiting from the beam splitter 45 and entering the high-sensitivity image sensor 60.

Figure 12:
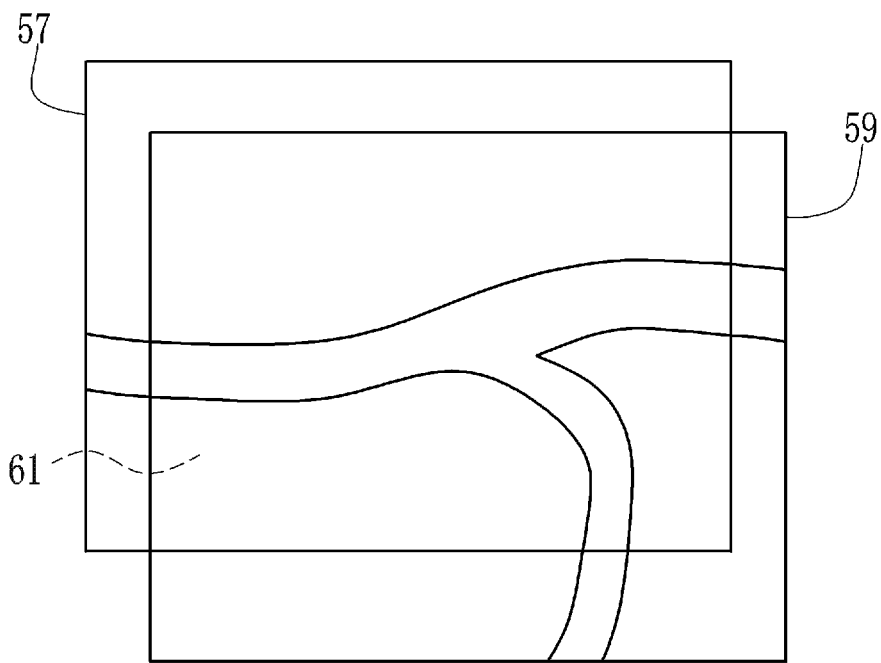
FIG. 12 is an explanatory view of an object image obtained by the normal image sensor, an object image obtained by the high-sensitivity image sensor, and an overlapping area of the object images.

However, if the optical paths are not equalized, as shown in FIG. 12, an object image 57 obtained by the normal image sensor 53 partly differs from an object image 59 obtained by the high-sensitivity image sensor 60. An overlapping area 61 is determined by AND operation of the object images 57 and 59. As shown in FIG. 8, in the light receiving surface 56 of the normal image sensor 53, a portion corresponding to the overlapping area 61 is referred to as an effective area 56b of the light receiving area 56a, which captures the reflected light and forms the object image 57. Likewise, as shown in FIG. 11, in the light receiving surface 62 of the high-sensitivity image sensor 60, a portion corresponding to the overlapping area 61 is referred to as an effective area 62b of the light receiving area 62a, which forms the object image 59. These effective areas 56b and 62b are preferably determined by checking the object image 57 outputted from the normal image sensor 53 and the object image 59 outputted from the high-sensitivity image sensor 60 on the monitor 14 after registration of the optical systems including the beam splitter 45. In a case where the high-sensitivity image sensor 60 has lower resolution than the normal image sensor 53, the length of the optical path of the high-sensitivity image sensor 60 may be slightly elongated because the high-sensitivity image sensor 60 does not need high sharpness.

As shown in FIG. 2, the processor device 12 includes the MPU 70, the DSPs 72 and 73, and a processor 75. The MPU 70 controls the operation of the electronic endoscope 11 and the light source device 13, in addition to the operation of the processor device 12. The MPU 70 has a control program memory 70a for storing various control programs and setup data. The control program written for observation of the oxygen saturation level is loaded from the control program memory 70a and executed to carry out various control operations. Note that, the control program memory 70a is rewritable. Instead of or in addition to the control program written for observation of the oxygen saturation level, for example, a control program for AFI (autofluorescence imaging) may be installed. Note that, an image signal outputted from the effective area 56b, 62b of the normal or high-sensitivity image sensor 53, 60 is used for producing the normal or special image. An image signal outputted from an area other than the effective area 56b, 62b is unused for producing the normal or special image.

The DSP 72 obtains the image signal outputted from the normal imaging unit 47. The DSP 72 applies signal processing including gamma correction and white balance correction to the image signal, to produce a normal-sensor image. The normal-sensor image includes first and second normal-sensor images. The first normal-sensor image is produced from NR, NG, and NB signals obtained by the normal image sensor 53 under irradiation with the NR, NG, and NB light. The second normal-sensor image is produced from SR, SG, and SB signals obtained by the normal image sensor 53 under irradiation with the SR, SG, and SB light. The first and second normal-sensor images are transmitted to the processor 75. The DSP 73 performs similar processing and produces a high-sensitivity-sensor image. The high-sensitivity-sensor image is produced from SR, SG, and SB signals obtained by the high-sensitivity image sensor 60 under irradiation with the SR, SG, and SB light. The produced high-sensitivity-sensor image is transmitted to the processor 75.

The DSPs 72 and 73 apply a pixel number conversion process to the first and second normal-sensor images and the high-sensitivity-sensor image. The pixel number conversion process converts a pixel pitch of the first and second normal-sensor images and the high-sensitivity-sensor image by using a spline function and the like. When the effective area 56b of the normal image sensor 53 has a pixel number of "n1×m1" and the effective area 62b of the high-sensitivity image sensor 60 has a pixel number of "n2×m2", the pixel number of a part of every image corresponding to the effective area 56b or 62b is converted into "n×m" by the pixel number conversion process. "n×m" may be equal to "n1×m1", "n2×m2", or a default value. The aspect ratio of a pixel is preferably the same between before and after the pixel number conversion process, but may be different. Even if the aspect ratio of the pixel is different, a part of every image corresponding to the effective area 56b or 62b has the same angle of view between before and after the pixel number conversion process.

The processor 75 includes a light amount evaluation section 78, a normal image processing section 79, and a special image processing section 80. In the special mode, the light amount evaluation section 78, which functions as a light amount measurement section, measures the amount of reflected light of the SR, SG, and SB light (hereinafter collectively called "special illumination light) based on the second normal-sensor image or the high-sensitivity-sensor image. Then, the light amount evaluation section 78 judges whether or not the measured light amount is enough to calculate the oxygen saturation level, in other words, whether or not the measured light amount is not low. Out of the special illumination light, the amount of reflected light of only the SB light may be measured to judge whether or not the measured light amount is not low. In this case, the light amount is measured based on the intensity of the SB signal.

The light amount evaluation section 78 measures the reflected light amount of the special illumination light based on an average (average pixel value) of pixel values outputted from all pixels of the entire light receiving surface 56, 62 of the normal image sensor 53 or the high-sensitivity image sensor 60, or pixels arranged in a middle portion (size of approximately ¼) of the light receiving surface 56, 62. At this time, an amplification factor has to be taken into consideration as for the high-sensitivity-sensor image. The larger the average pixel value, the larger the reflected light amount. The light amount evaluation section 78 compares the average pixel value with a predetermined sensor selection threshold value, to judge whether or not the reflected light amount is not low. Note that, the sensor selection threshold value is preferably set at ¹⁄₅₀ of the maximum sensitivity of the normal image sensor 53. For example, when the maximum sensitivity is 10-bit 1024-level, the sensor selection threshold value is set at 20.

The reflected light amount of the special illumination light may be measured from pixel values of a specific color component of the second normal-sensor image or the high-sensitivity-sensor image, e.g. an average of pixel values of a B image. Alternatively, the reflected light amount may be measured from arbitrarily weighted pixel values of a plurality of color components of the second normal-sensor image or the high-sensitivity-sensor image, e.g. by weighting at 2:2:1 the pixel values of the B image, pixel values of a G image, and pixel values of an R image.

When the reflected light amount of the special illumination light is not judged to be low, only the normal image sensor 53 is used. As shown in FIG. 13A, the normal image sensor 53 sequentially captures images of the internal body portion irradiated with the NR, NG, and NB light (hereinafter collectively called "normal illumination light") and the special illumination light. The normal image sensor 53 performs imaging operation during each emission period of the normal illumination light, and readout operation in each shading period. Thus, as shown in FIG. 13B, NR, SR, NG, SG, NB, and SB signals are read out from the normal image sensor 53.

When the reflected light amount of the special illumination light is judged to be low, both the normal image sensor 53 and the high-sensitivity image sensor 60 are used. As shown in FIG. 14A, the normal image sensor 53 captures images under irradiation with the normal illumination light, while the high-sensitivity image sensor 60 captures images under irradiation with the special illumination light. The normal image sensor 53 performs the imaging operation during each emission period of the normal illumination light, and readout operation in the shading period provided after each emission period of the normal illumination light. The normal image sensor 53 performs reset operation in the shading period provided after each emission period of the special illumination light, in order to discharge electric charge produced by photoelectric conversion of the special illumination light. On the other hand, the high-sensitivity image sensor 60 performs the imaging operation during each emission period of the special illumination light, and the readout operation in the shading period provided after each emission period of the special illumination light. The high-sensitivity image sensor 60 performs the reset operation in the shading period provided after each emission period of the normal illumination light, in order to discharge electric charge produced by photoelectric conversion of the normal illumination light.

Accordingly, as shown in FIG. 14B, the NR, NG, and NB signals are read out from the normal image sensor 53, while the SR, SG, and SB signals are read out from the high-sensitivity image sensor 60.

Figure 15:
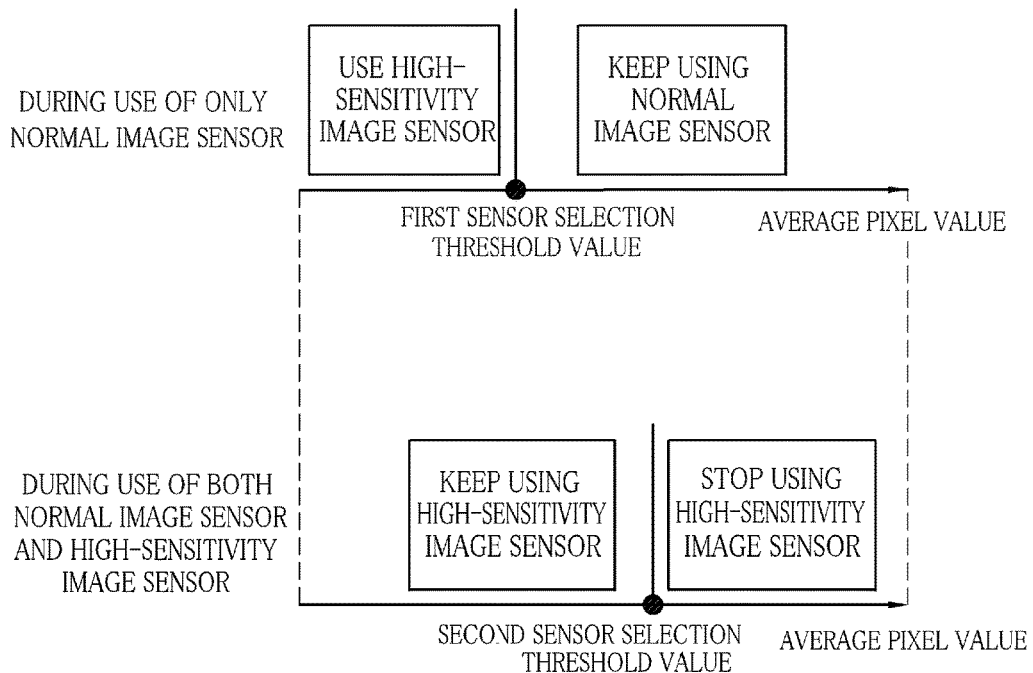
FIG. 15 is an explanatory view of the relation between first and second sensor selection threshold values.

The light amount evaluation section 78 may determine which sensor to use based on two sensor selection threshold values. In this case, as shown in FIG. 15, first and second sensor selection threshold values are set in advance. The second sensor selection threshold value is larger than the first sensor selection threshold value. For example, the second sensor selection threshold value is set at ⅕ of the maximum sensitivity, while the first sensor selection threshold value is set at ¹⁄₅₀ of the maximum sensitivity. In a case where only the normal image sensor 53 is used, when the average pixel value of the second normal-sensor image is the first sensor selection threshold value or less, the use of the high-sensitivity image sensor 60 is started. The high-sensitivity image sensor 60 captures the images under irradiation with the special illumination light, while the normal image sensor 53 captures the images under irradiation with the normal illumination light. On the other hand, in a case where both the normal image sensor 53 and the high-sensitivity image sensor 60 are used, when the average pixel value of the high-sensitivity-sensor image is the second sensor selection threshold value or more, the use of the high-sensitivity image sensor 60 is stopped. The normal image sensor 53 captures the images under irradiation with the normal and special illumination light.

In the case of using the high-sensitivity image sensor 60, a binning process may be applied to further sensitize the image signal obtained by the high-sensitivity image sensor 60. In the binning process, as shown in FIG. 9, a binning processor 70b of the MPU 70 controls the high-sensitivity image sensor 60. As the binning process, hardware binning is adopted in which pixel addition is performed within the high-sensitivity image sensor 60, but software binning may be adopted instead in which outputted signals are subjected to the pixel addition. In the hardware binning, a drive signal for driving the high-sensitivity image sensor 60 is modified. In the binning process, the pixel area obtained by the pixel addition does not necessarily have the same number of pixels between its length and width directions. For example, the pixel area may have two pixels in the length direction and one pixel in the width direction, or four pixels in the length direction and one pixel in the width direction.

Whether or not to perform the binning process is determined based on the reflected light amount of the special illumination light. The light amount evaluation section 78 has a binning start threshold value and a binning stop threshold value. The binning stop threshold value is preferably larger than the binning start threshold value. For example, the binning stop threshold value is set at "(binning start threshold value)×¹⁄₆+10". If the difference between the binning start and stop threshold values is small, switching between performing and not performing the binning process occurs too often. Thus, it is preferable that the binning start and stop threshold values are set so as to keep an appropriate switching frequency.

As shown in FIG. 10, during the stop of the binning process, the image signal is read out in a read unit of 1×1 pixel without performing the binning process, as long as the average pixel value of the high-sensitivity-sensor image obtained by the high-sensitivity image sensor 60 is the binning start threshold value or more. When the average pixel value is less than the binning start threshold value, the binning process is started, and the image signal is read out in a read unit of 4×4 pixels, for example. During the execution of the binning process, the binning process is continued as long as the average pixel value of the high-sensitivity-sensor image is less than the binning stop threshold value. When the average pixel value is the binning stop threshold value or more, the binning process is stopped, and the image signal is read out in the read unit of 1×1 pixel without performing the binning process.

Note that, the level of the binning process, in other words, the number of lengthwise and widthwise pixels being the read unit of the image signal is arbitrary changeable in accordance with the average pixel value of the high-sensitivity-sensor image. More specifically, the smaller the average pixel value, the larger the level of the binning process is set. For example, when the average pixel value is less than ⅕ of the maximum sensitivity, the binning process is performed in a read unit of 2×2 pixels. When the average pixel value is further reduced to less than ¹⁄₅₀, the binning process is performed in a read unit of 4×4 pixels.

As described above, with the use of the first and second sensor selection threshold values and the binning start and stop threshold values, the use of only the normal image sensor 53 may be switched to the use of the high-sensitivity image sensor 60, and furthermore the absence of the binning process may be switched to the presence of the binning process in accordance with reduction in the reflected light amount of the special illumination light.

Note that, FIGS. 13A, 13B, 14A, and 14B show imaging operation using the FT type image sensor, in which the shading period for electric charge transfer is necessarily provided between the adjacent emission periods of the illumination light. In the case of using the FIT or IT type image sensor, as shown in FIGS. 13C and 14C, the shading period is unnecessary. FIG. 13C, corresponding to FIG. 13A, shows the imaging operation in a case where the reflected light amount of the special illumination light is not low. FIG. 14C, corresponding to FIG. 14A, shows the imaging operation in a case where the reflected light amount of the special illumination light is low.

The normal image processing section 79 assigns the B, G, and R images of the first normal-sensor image outputted from the DSP 72 to B, G, and R channels of the monitor 14, respectively, so the normal image is displayed on the monitor 14. Since the B, G, and R images of the first normal-sensor image are captured at different times, these images are preferably registered with each other by pattern matching or the like.

Figure 16:
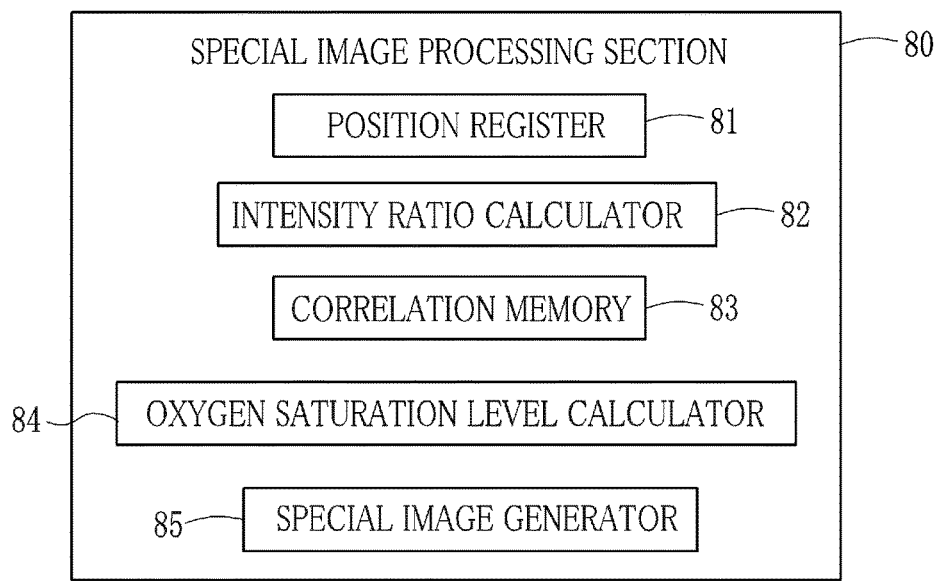
FIG. 16 is a block diagram of a special image processing section.

As shown in FIG. 16, the special image processing section 80 includes a position register 81, an intensity ratio calculator 82, a correlation memory 83, an oxygen saturation level calculator 84, and a special image generator 85. The position register 81 performs positional registration among the B, G, and R images of the second normal-sensor image obtained by the normal image sensor 53 or the high-sensitivity-sensor image obtained by the high-sensitivity image sensor 60. In the positional registration, a matching process is preferably performed so that a blood vessel pattern of the B, G, and R images coincides with each other.

To obtain the oxygen saturation level from the second normal-sensor image or the high-sensitivity-sensor image, the intensity ratio calculator 82 calculates an intensity ratio B/G between the B and G images of the second normal-sensor image or the high-sensitivity-sensor image and an intensity ratio R/G between the G and R images thereof. The intensity ratio calculator 82 calculates the intensity ratios B/G and R/G on a pixel-by-pixel basis by using the intensity of the pixel situated in the same position in the B and G images and in the R and G images. The intensity ratios are calculated as to every pixel included in the image signal, but may be calculated as to only pixels situated in a blood vessel area. In this case, the blood vessel area is determined based on difference in the pixel value between the blood vessel area and the other area.

Figure 17:
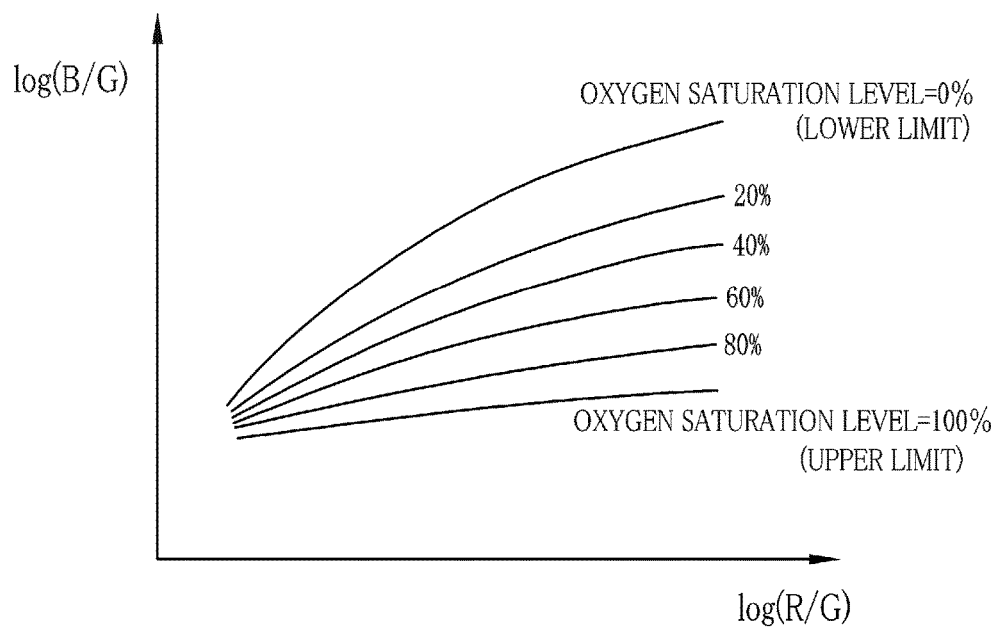
FIG. 17 is a graph showing the correlation among intensity ratios B/G and R/G and an oxygen saturation level.

The correlation memory 83 stores the correlation among the intensity ratios B/G and R/G and the oxygen saturation level. As shown in FIG. 17, the correlation takes the form of a two-dimensional table in which contour lines representing the oxygen saturation level are defined in two-dimensional space. The position and shape of the contour lines are determined by physical simulation of light scattering, and variable in accordance with blood volume. For example, variation in the blood volume widens or narrows the distance between the contour lines next to each other. Note that, the intensity ratios B/G and R/G are stored in log scale.

The correlation is closely related to the light absorption property of oxyhemoglobin HbO and deoxyhemoglobin Hb (see FIG. 6) and the light scattering property of mucosa. For example, the use of a wavelength of 473 nm at which the absorption coefficient much differs between oxyhemoglobin HbO and deoxyhemoglobin Hb allows the obtainment of information about the oxygen saturation level. However, the B image including a wavelength component of 473 nm is highly dependent not only on the oxygen saturation level but also on the blood volume. Thus, the use of the R image, which corresponds to light mainly dependent on the blood volume, and the G image, which is a reference image (standardization signal) of the B and R images, in addition to the B image, allows the obtainment of the oxygen saturation level with high accuracy with eliminating the influence of the blood volume.

As shown in FIG. 17, the intensity ratio B/G increases with increase in the intensity ratio R/G. In other words, the contour line representing an oxygen saturation level of 0% ascends slantly. The reason for this is as follows. The blood volume increases with increase in the intensity ratio R/G due to the correlation therebetween. Out of the B, G, and R images, a signal value of the G image decreases most greatly with increase in the blood volume, and a signal value of the B image decreases next greatly. This is because the absorption coefficient is higher at a wavelength band of 540 to 580 nm included in the G image than that at a wavelength band of around 470 nm included in the B image (see FIG. 6). Therefore, as for the intensity ratio B/G, with increase in the blood volume, an intensity value of G being a denominator decreases more greatly than that of the B being a numerator. In other words, the intensity ratio B/G increases with increase in the blood volume.

The oxygen saturation level calculator 84 calculates the oxygen saturation level of each pixel with the use of the correlation stored in the correlation memory 83 and the intensity ratios B/G and R/G obtained by the intensity ratio calculator 82. To be more specific, when B*, G*, and R* represent intensity values of a certain pixel of the B, G, and R images of the second normal-sensor image or the high-sensitivity-sensor image, the intensity ratio calculator 82 calculates intensity ratios B*/G* and R*/G*.

Figure 18:
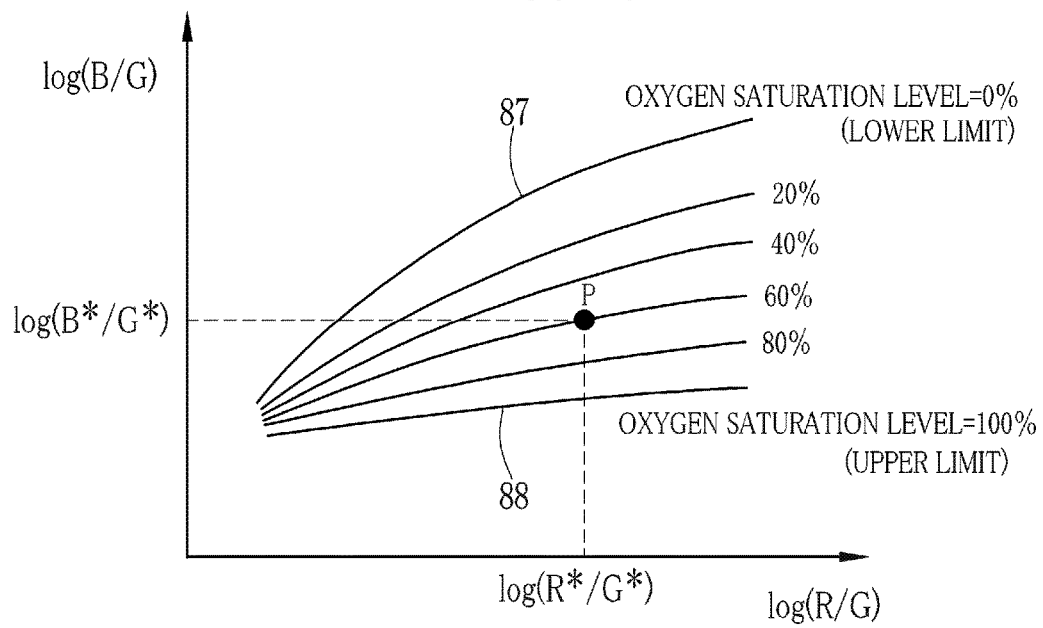
FIG. 18 is a graph that explains a calculation method of the oxygen saturation level using the correlation of FIG. 17.

As shown in FIG. 18, a point P corresponding to the signal ratios B*/G* and R*/G* is determined in the correlation stored in the correlation memory 83. When the point P is situated between a lower limit line 87 representing an oxygen saturation level of 0% and an upper limit line 88 representing an oxygen saturation level of 100%, the point P indicates the percentile of the oxygen saturation level. Taking FIG. 18 as an example, the point P is positioned in a contour line of 60%, so the oxygen saturation level is 60%.

If the point is positioned above the lower limit line 87, the oxygen saturation level is determined to be 0%. If the point is positioned below the upper limit line 88, the oxygen saturation level is determined to be 100%. Note that, if the point is out of the range between the lower limit line 87 and the upper limit line 88, the oxygen saturation level of the point may be judged to be unreliable and not be displayed on the monitor 14.

Figure 19A:
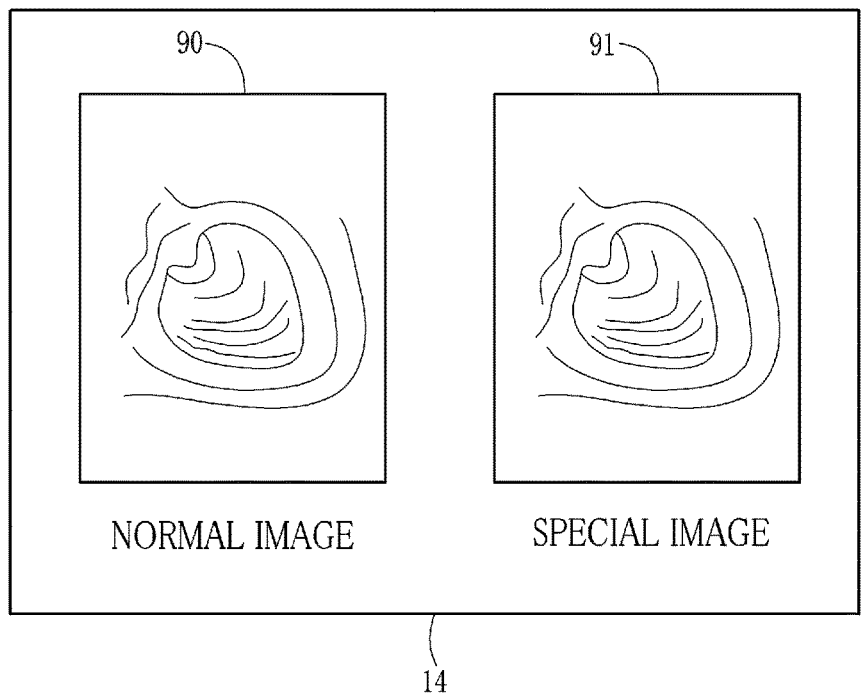
FIG. 19A is a plan view of a monitor in which a normal image and a special image are displayed side by side.
Figure 19B:
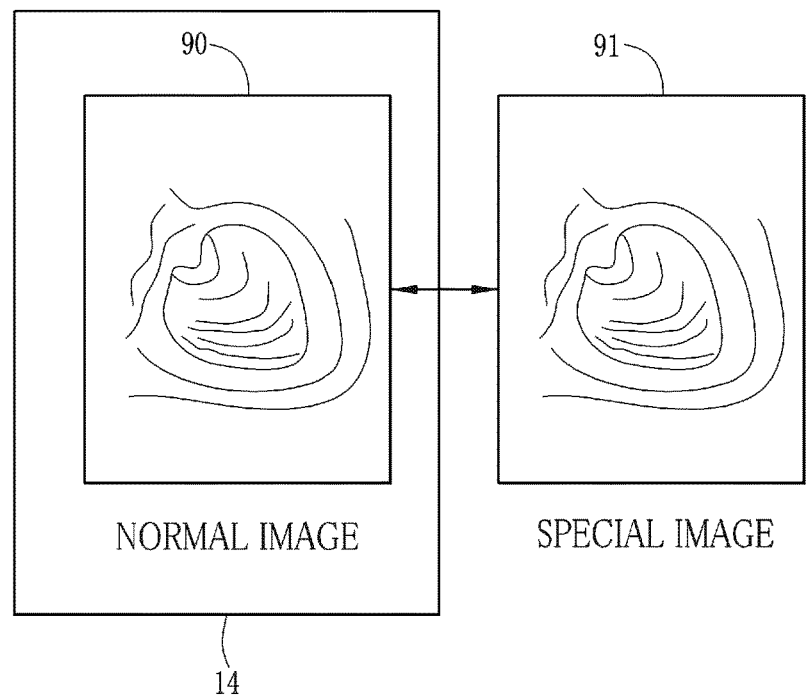
FIG. 19B is a plan view of the monitor in which the normal image or the special image is displayed selectively.

The special image generator 85 produces the special image based on the oxygen saturation level obtained by the oxygen saturation level calculator 84. The special image may be a whole artificial color image in which the entire normal image is colored with artificial colors in accordance with the degree of the oxygen saturation level, or a partly artificial color image in which only a hypoxic region having the oxygen saturation level less than a certain value is colored artificially while the other region colored normally. The produced special image is displayed on the monitor 14. As a way to display, a normal image 90 and a special image 91 may be displayed concurrently side-by-side on the monitor 14 as shown in FIG. 19A, or may be displayed alternately on the monitor 14 as shown in FIG. 19B.

In the first embodiment, the NR, SR, NG, SG, NB, and SB light is applied in this order in the special mode, but the order is not limited to this. For example, the NR, NG, and NB light may be applied first, and then the SR, SG, and SB light may be applied.

In the first embodiment, only the high-sensitivity image sensor 60 performs the binning process, but the normal image sensor 53 may perform the binning process when the special illumination light is incident thereon. A threshold value that is used for commanding the normal image sensor 53 to start the binning process is preferably set higher than the above binning start threshold value (the threshold value used for commanding the high-sensitivity image sensor 60 to start the binning process).

The CCD image sensors are used in the normal imaging unit 47 and the high-sensitivity imaging unit 49 in the above embodiment, but CMOS image sensors may be used in a like manner.

Second Embodiment

In a second embodiment, the NG and NR light is used instead of the SC and SR light of the first embodiment, as illumination light necessary for producing the special image. The other configuration is the same as that of the first embodiment, so only difference from the first embodiment will be described below.

Figure 20:
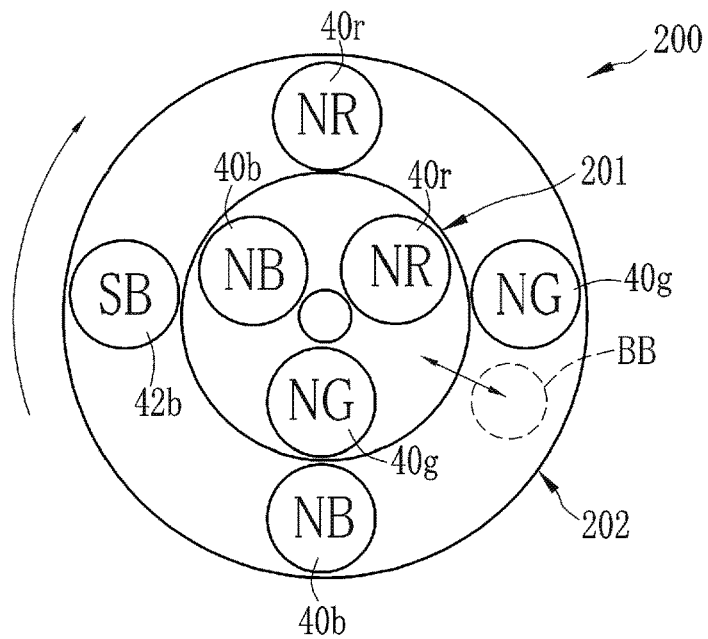
FIG. 20 is a top plan view of a rotary filter according to a second embodiment.

Referring to FIG. 20, as with the first embodiment, a rotary filter 200, having an inner radial portion 201 and an outer radial portion 202, is shifted in the normal mode to the inner position in which the inner radial portion 201 is disposed in the optical path of the broad band light BB. In the special mode, the rotary filter 200 is shifted to the outer position in which the outer radial portion 202 is disposed in the optical path of the broad band light BB. The inner radial portion 201 has the same structure as the inner radial portion 35 of the rotary filter 31 of the first embodiment. Note that, the rotary filter 200 having the light shielding portions is necessary used in the case of using the FT type CCD image sensor, but another rotary filter without having the light shielding portions is adoptable in the case of using the FIT or IT type image sensor.

On the contrary, the outer radial portion 202, which has different structure from that of the outer radial portion 37 of the rotary filter 31 of the first embodiment, does not have the SR filter 42*r* and the SG filter 42*g*. The outer radial portion 202 is formed with four filters i.e. the NR filter 40*r*, the NG filter 40*g*, the NB filter 40*b*, and the SB filter 42*b* arranged in its circumferential direction. The light shielding portion is formed between two of the filters 40*r*, 40*g*, 40*b*, and 42*b* adjoining each other to block the broad band light BB.

Figure 21:
FIG. 21 is an explanatory view showing an emission pattern in the special mode according to the second embodiment.

Accordingly, in the special mode, as shown in FIG. 21, the rotation of the rotary filter 200 set in the outer position allows the emission of the NR, NG, NB, and SB light in this order to the internal body portion. The shading period is provided after each emission period.

Figure 22:
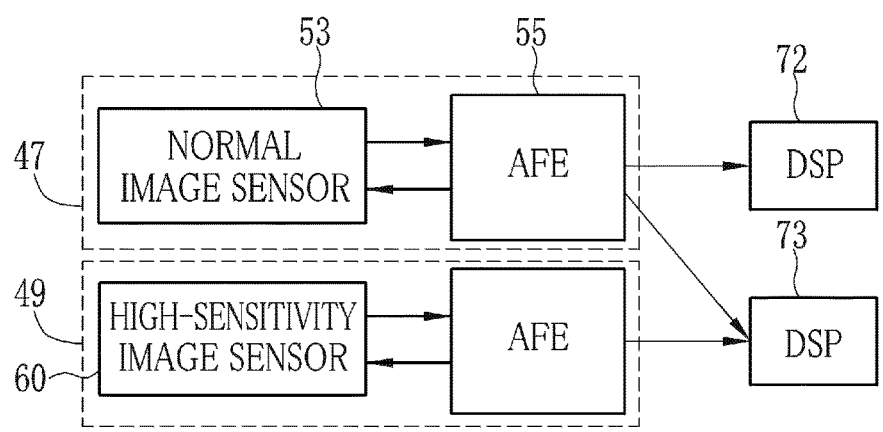
FIG. 22 is an explanatory view of input and output of image signals among a normal imaging unit, a high-sensitivity imaging unit, a normal DSP, and a high-sensitivity DSP.

In the second embodiment, the DSP 72 produces the first normal-sensor image from the NR, NG, and NB signals inputted from the AFE 55 of the normal imaging unit 47. The DSP 72 produces the second normal-sensor image from the NR, NG, SB signals inputted from the AFE 55 of the normal imaging unit 47. As shown in FIG. 22, in the second embodiment, the AFE 55 of the normal imaging unit 47 inputs the imaging signals not only to the DSP 72 but also to the DSP 73. In contrast to the first embodiment, the DSP 73 produces the high-sensitivity-sensor image from the NR and NG signals inputted from the AFE 55 of the normal imaging unit 47 and the SB signal inputted from the AFE 55 of the high-sensitivity imaging unit 49.

In the special mode, the light amount evaluation section 78 of the second embodiment measures the reflected light amount of the SB light based on the B image of the second normal sensor image or the high-sensitivity-sensor image. The light amount evaluation section 78 judges whether or not the reflected light amount of the SB light is enough to reliably calculate the oxygen saturation level, in other words, is not low.

Figure 23:
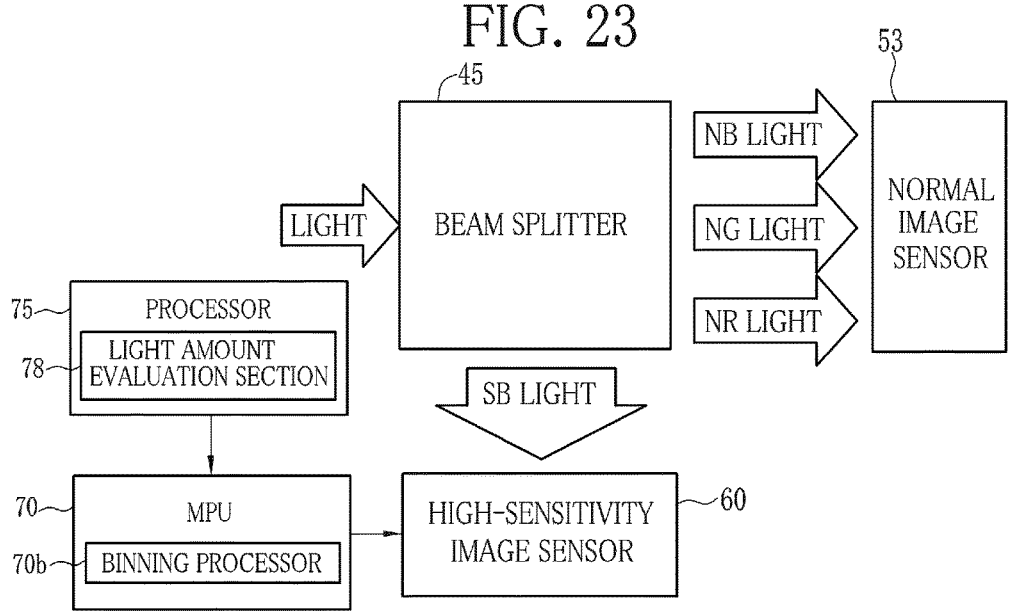
FIG. 23 is an explanatory view of a binning process in the second embodiment.

The binning process is performed as follows in the second embodiment. As shown in FIG. 23, the light amount evaluation section 78 calculates the average pixel value based on the high-sensitivity-sensor image obtained under irradiation with the SB light. The start and stop of the binning process are controlled in a like manner as the first embodiment by comparing the average pixel value with the binning start and stop threshold values.

In the second embodiment, when the high-sensitivity image sensor 60 performs the binning process, it is necessary to equalize the pixel number of the NR and NG signals outputted from the normal image sensor 53 with the pixel number of the SB signal outputted from the high-sensitivity image sensor 60. This is because not only the SB signal but also the NR and NG signals are used to produce the special image. The equalization of the pixel number among the NR, NG, and SB signals allows close agreement between an image of an object produced by the NR and NG signals and an image of the object produced by the SB signal. A display area of the NR and NG signals coincides with a display area of the SB signal.

Figure 24:
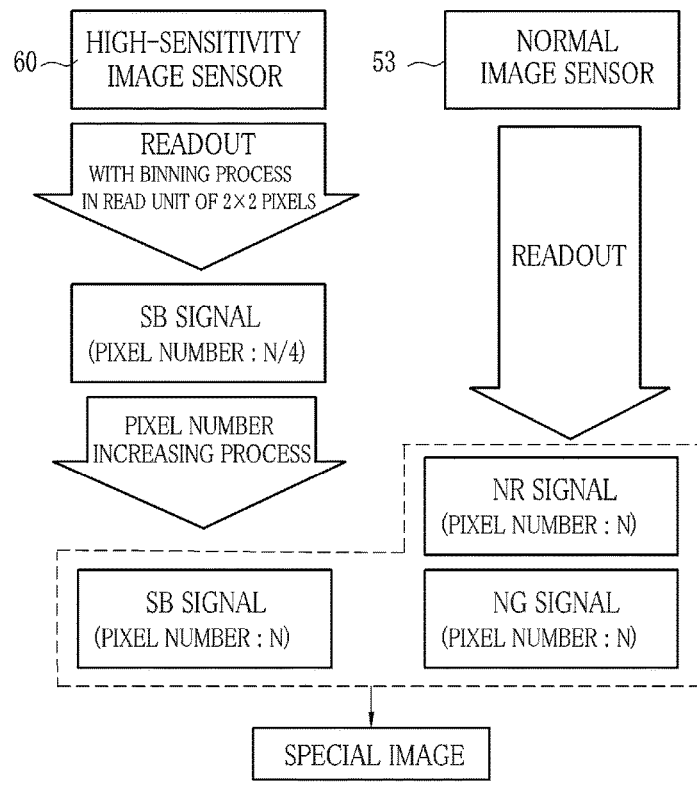
FIG. 24 is an explanatory view of a process of equalizing a pixel number between an SB signal after being subjected to the binning process by the high-sensitivity image sensor and NR and NG signals outputted from the normal image sensor.

For example, as shown in FIG. 24, when the pixel number of the NR and NG signals is represented by "N", the pixel number of the SB signal after being subjected to the binning process in a unit of 2×2 pixels becomes "N/4". At this time, the pixel number of the SB signal is multiplied by 4 by a pixel number increasing process, or the pixel number of the NR and NG signals is multiplied by ¼ by a pixel number decreasing process, in order to equalize the pixel number of the NR, NG, and SB signals. The special image is produced from the NR, NG, and SB signals having the same pixel number.

Figure 25:
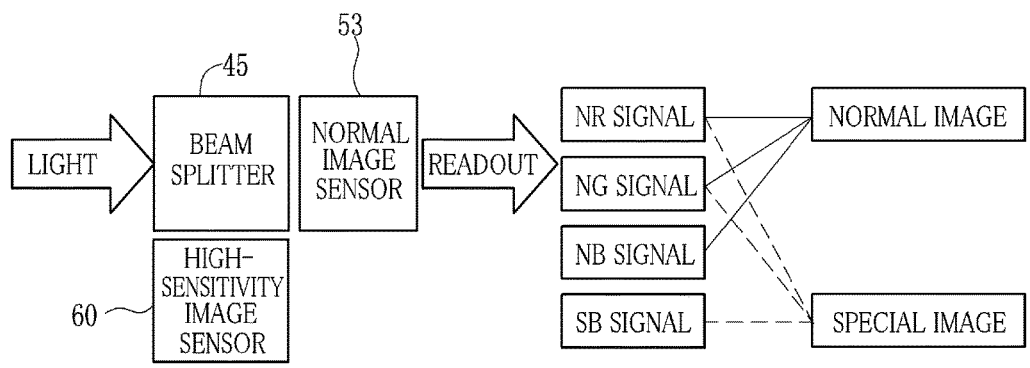
FIG. 25A is a timing chart showing imaging and readout timing in a case where the light amount of the reflected special light is not judged to be low in the second embodiment.
FIG. 25B is an explanatory view of output of normal signals and special signals in a case where the light amount is not judged to be low.
FIG. 25C is a timing chart in the case of using the FIT or IT type monochrome high-sensitivity image sensor.

In the second embodiment, the switching between the normal image sensor 53 and the high-sensitivity image sensor 60 is performed as follows. As shown in FIG. 25A, the normal image sensor 53 captures the image of the internal body portion irradiated with the SB light, as long as the reflected light amount of the SB light is not judged to be low. Thus, the NR, NG, NB, and SB signals are read out in this order from the normal image sensor 53.

Figure 26:
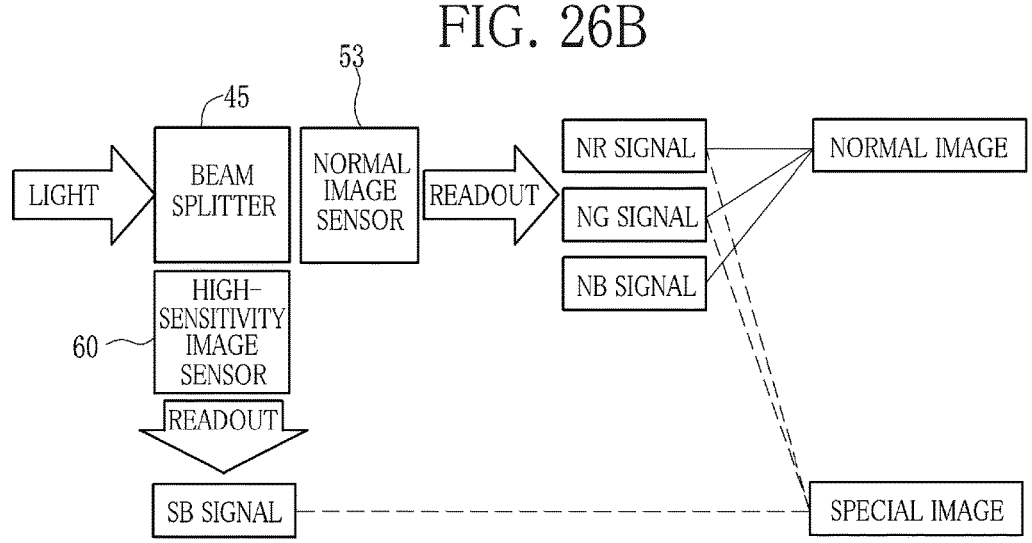
FIG. 26A is a timing chart of imaging and readout timing in a case where the light amount of the reflected special light is judged to be low in the second embodiment.
FIG. 26B is an explanatory view of output of the normal signals and the special signals in a case where the light amount is judged to be low.
FIG. 26C is a timing chart in the case of using the FIT or IT type monochrome high-sensitivity image sensor.

When the light amount evaluation section 78 judges that the reflected light amount of the SB light is low, as shown in FIG. 26A, the high-sensitivity image sensor 60, instead of the normal image sensor 53, captures the image under irradiation with the SB light. The normal image sensor 53 performs the imaging operation during each emission period of the NR, NG, and NB light, and readout operation in the shading period provided after each emission period. The normal image sensor 53 performs reset operation in the shading period provided after the emission period of the SB light, in order to discharge electric charge produced by photoelectric conversion of the SB light. On the other hand, the high-sensitivity image sensor 60 performs the imaging operation only during the emission period of the SB light, and the readout operation of the SB signal in the shading period provided after the emission period of the SB light. The high-sensitivity image sensor 60 performs the reset operation in the shading period provided after the emission period of the NB light, in order to discharge electric charge produced by photoelectric conversion of the NR, NG, and NB light.

Accordingly, as shown in FIG. 26B, the NR, NG, and NB signals are read out from the normal image sensor 53, while the SB signal is read out from the high-sensitivity image sensor 60. The normal image is produced from the NR, NG, and NB signals. The special image is produced from the NR, NG, and SB signals. A method for producing the normal image and the special image is the same as that of the first embodiment.

Note that, FIGS. 25A, 25B, 26A, and 26B show imaging operation using the FT type image sensor, in which the shading period for electric charge transfer is necessarily provided between the adjacent emission periods of the illumination light. In the case of using the FIT or IT type image sensor, as shown in FIGS. 25C and 26C, the shading period is unnecessary. FIG. 25C, corresponding to FIG. 25A, shows the imaging operation in a case where the reflected light amount of the SB light is not low. FIG. 26C, corresponding to FIG. 26A, shows the imaging operation in a case where the reflected light amount of the SB light is low.

Figures 27, 28A, 28B:
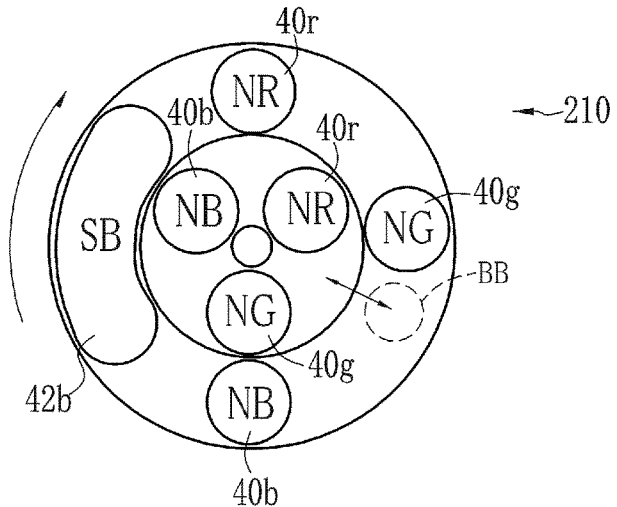
FIG. 27 is a top plan view of another rotary filter according to the second embodiment.
FIG. 28A is a timing chart with the use of the rotary filter of FIG. 27 in which the imaging and readout timing is shown in a case where the light amount of the reflected special light is not judged to be low.
FIG. 28B is a timing chart with the use of the rotary filter of FIG. 27 in which the imaging and readout timing is shown in a case where the light amount of the reflected special light is judged to be low.

In the second embodiment, another rotary filter 210 having a large SB filter 42b, as shown in FIG. 27, may be used instead of the rotary filter 200. The use of the rotary filter 210 makes the emission period of the SB light longer than the emission periods of the other NR, NG, and NB light. Thus, the image is captured with higher sensitivity during the emission period of the SB light. The rotary filter 210 having the shielding portions, as shown in FIG. 27, is necessarily used in the case of adopting the FT type CCD image sensor, but a rotary filter without having the shielding portion is usable in the case of adopting the FIT or IT type image sensor.

In the case of using the rotary filter 210, as shown in FIGS. 28A and 28B, either of the normal image sensor 53 and the high-sensitivity image sensor 60 performs the imaging operation under irradiation with the SB light for longer time than time of the imaging operation under irradiation with the NR, NG, and NB light. FIGS. 28A and 28B show the imaging operation using the FT type image sensor, in which the shading period for electric charge transfer is necessarily provided between the adjacent emission periods of the illumination light. In the case of using the FIT or IT type image sensor, as shown in FIGS. 28C and 28D, the shading period is unnecessary. FIGS. 28A and 28C show the imaging operation in a case where the reflected light amount of the SB light is not low. FIGS. 28B and 28D show the imaging operation in a case where the reflected light amount of the SB light is low.

In the second embodiment, the NR, NG, NB, and SB light is emitted in this order in the special mode, but the order is not limited to this.

Third Embodiment

Figure 29:
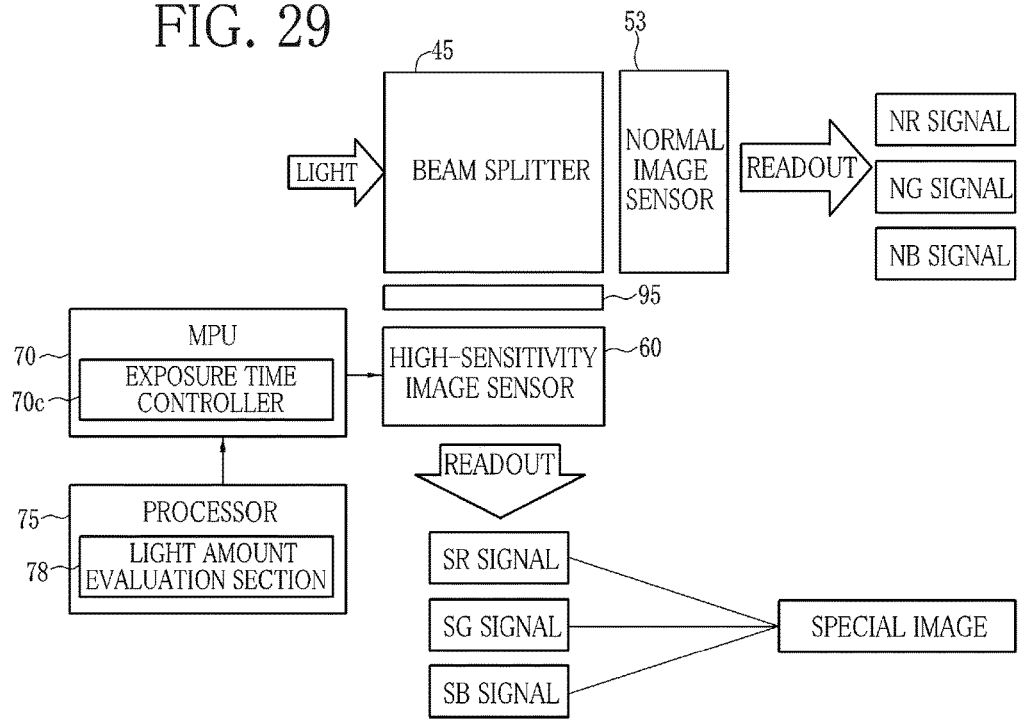
FIG. 29 is an explanatory view of extension of exposure time in a case where the light amount is judged to be low.

In a third embodiment, exposure time of the high-sensitivity image sensor 60 is extended in order to increase the sensitivity of the image signals used for producing the special image. In the third embodiment, as shown in FIG. 29, a shutter 95 is provided between the beam splitter 45 and the high-sensitivity image sensor 60 to control the exposure time. The operation of the shutter 95 is controlled by an exposure time controller 70c of the MPU 70.

The following description describes exposure time control in the case of producing the special image from the SR, SG, and SB signals (refer to the first embodiment), but exposure time control in the case of producing the special image from the NR, NG, and SB signals (refer to the second embodiment) can be performed in a like manner. Note that, the third embodiment is the same as or similar to the first and second embodiments except for the binning process, so the description of the same configuration as those of the first and second embodiments will be omitted.

As shown in FIG. 29, the light amount evaluation section 78 of the processor 75 calculates the average pixel value based on the high-sensitivity-sensor image (image produced from the SR, SG, and SB signals). The average pixel value is compared with an extension start threshold value or an extension stop threshold value set in advance. The extension stop threshold value is preferably set larger than the extension start threshold value. For example, the extension stop threshold value is four times as large as the extension start threshold value.

Figure 30:
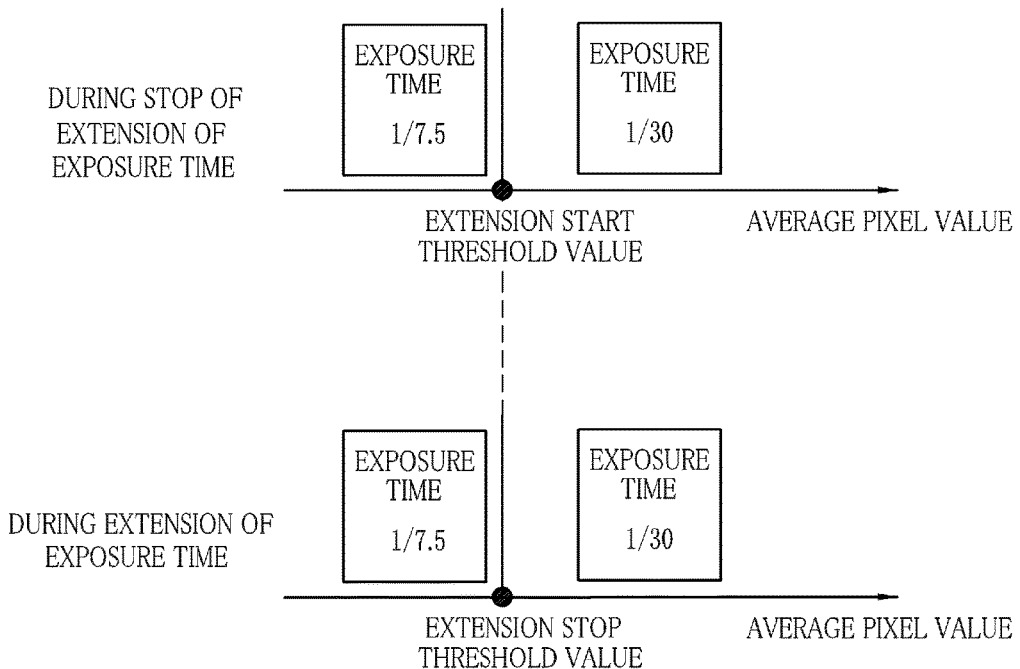
FIG. 30 is an explanatory view of the relation between extension start and stop threshold values.

As shown in FIG. 30, while the exposure time is not extended, the exposure time is set at $1/30$ seconds. This exposure time ($1/30$ seconds) is maintained, as long as the average pixel value of the high-sensitivity-sensor image is larger than the extension start threshold value. When the average pixel value is less than the extension start threshold value, the exposure time is extended from $1/30$ seconds to $1/7.5$ seconds by control of the shutter 95. In other words, the extension of the exposure time is started. While the exposure time is extended, the exposure time is set at $1/7.5$ seconds. This exposure time ($1/7.5$ seconds) is maintained, as long as the average pixel value is less than the extension stop threshold value. When the average pixel value is more than the extension stop threshold value, the exposure time is returned to $1/30$ seconds. How much the exposure time is to be extended is arbitrarily changeable in accordance with the average pixel value of the high-sensitivity-sensor image.

Note that, in the third embodiment, with the use of the extension start and stop threshold values and additionally the first and second sensor selection threshold values described in the first embodiment, the use of only the normal image sensor 53 may be switched to the use of the high-sensitivity image sensor 60 and furthermore to the extension of the exposure time in accordance with reduction in the reflected light amount of the special illumination light. Moreover, with the use of the binning start and stop threshold values described in the second embodiment in addition to the above threshold values, the use of only the normal image sensor 53 may be switched to the use of the high-sensitivity image sensor 60, to the use of one of the extension of the exposure time and the start of the binning process, and furthermore to the use of both of the extension of the exposure time and the start of the binning process in accordance with reduction in the reflected light amount of the special illumination light.

In the third embodiment, the exposure time is extended in the high-sensitivity image sensor 60, but the extension of the exposure time may be performed in the normal image sensor 53 in the case of producing the special image from the SR, SG, and SB signals outputted from the normal image sensor 53. In this case, as with above, a shutter 95 is provided between the beam splitter 45 and the normal image sensor 53, and the extension of the exposure time is performed only when the SB light is incident thereon. A threshold value that is used for starting the extension of the exposure time in the normal image sensor 53 is preferably set higher than the extension start threshold value described above.

Any one of the extension of the exposure time and the binning process may be selectively carried out. In this case, one of the binning process and the extension of the exposure time is selected in accordance with object distance (near view or far view). In the case of the far view, for example, the extension of the exposure time is preferably selected instead of the binning process, which causes reduction of resolution. In the case of the near view, on the other hand, the binning process is preferably performed.

Fourth Embodiment

Figure 31:
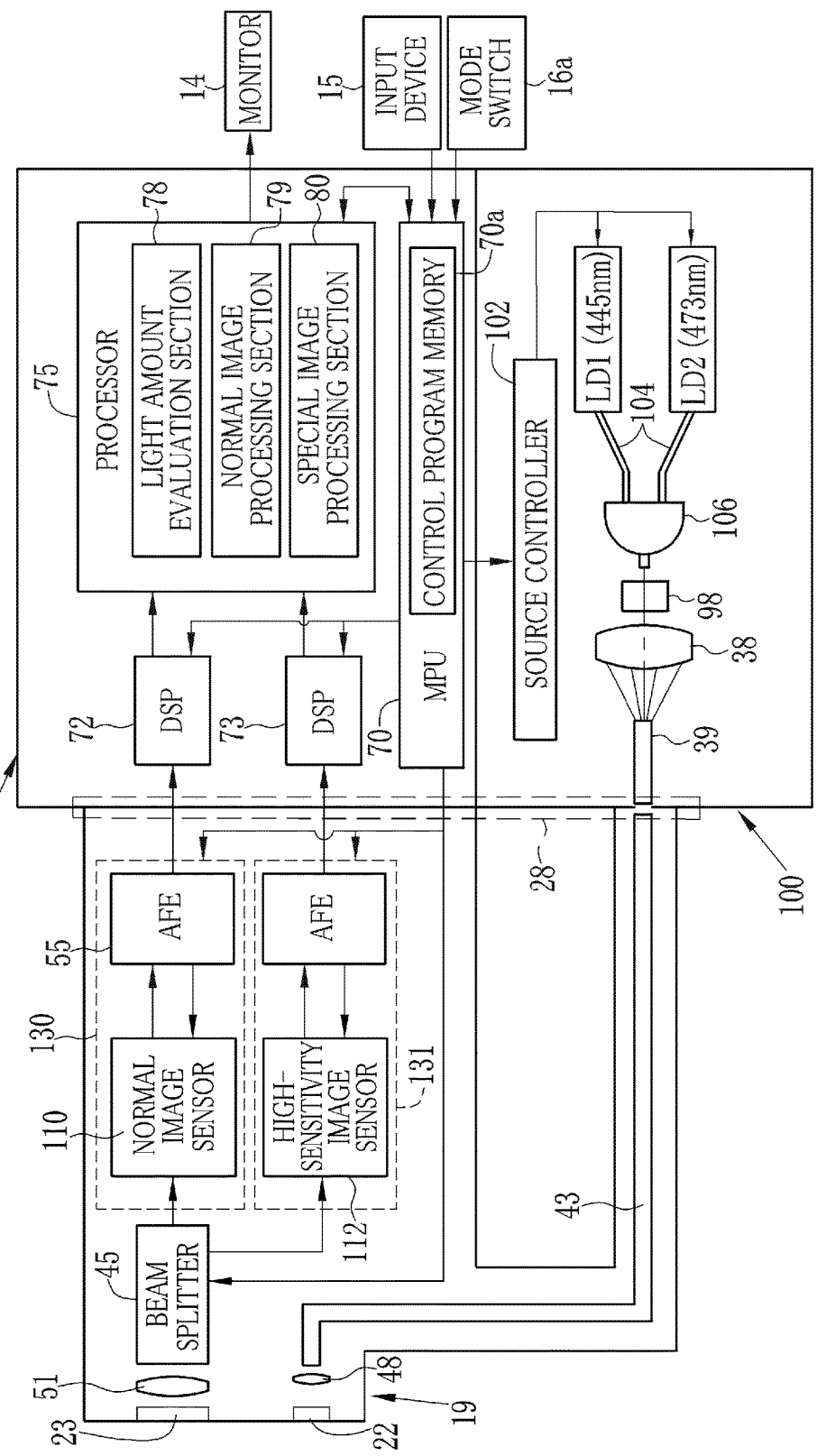
FIG. 31 is a block diagram of an endoscope system according to a fourth embodiment.

In the above embodiments, the illumination light is produced using the light source device 13 having the rotary filter. Instead of the light source device 13, as shown in FIG. 31, a light source device 100 that is constituted of laser beam sources LD1 and LD2, a phosphor 98, and a source controller 102 for controlling the operation of laser beam sources LD1 and LD2 may be used to produce the illumination light. In the case of using the light source device 100, a normal imaging unit 130 that is provided with a simultaneous type color normal image sensor 110 having RGB color filters is used instead of the monochrome normal image sensor 53. Likewise, a high-sensitivity imaging unit 131 that is provided with a simultaneous type color high-sensitivity image sensor 112 having RGB color filters is used instead of the monochrome high-sensitivity image sensor 60. The color normal image sensor 110 and the color high-sensitivity image sensor 112 are IT (inter transfer) type image sensors having an electronic shutter.

Figure 32:
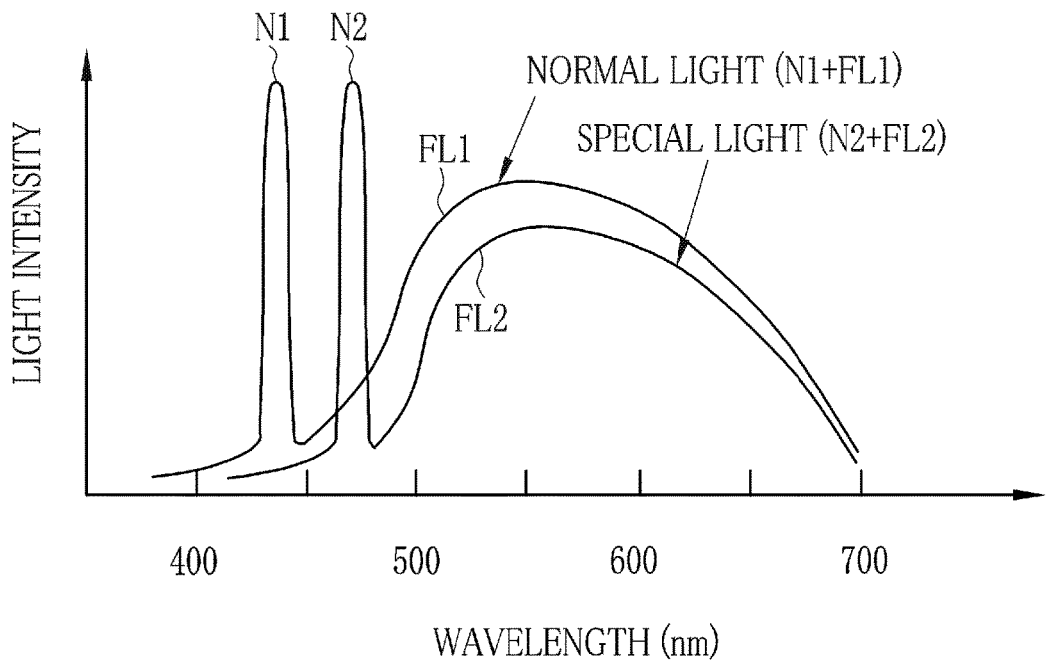
FIG. 32 is a graph showing emission spectra of the normal light and the special light according to the fourth embodiment.

As shown in FIG. 32, the laser beam source LD1 emits a laser beam N1 having a wavelength of 440±10 nm. The laser beam source LD2 emits a laser beam N2 having a wavelength of 470±10 nm. As the laser beam sources LD1 and LD2, InGaN, InGaNAs, or GaNAs laser diodes are available. The laser beams N1 and N2 are led to a combiner 106 through optical fibers 104. The combiner 106, being an optical element having the function of combining light beams transmitted through the optical fibers 104, combines optical axes of light beams that are incident selectively from the optical fibers 104 into one. The phosphor 98 is disposed downstream from the combiner 106. Instead of the laser beam sources LD1 and LD2, LEDs (light emitting diodes) may be used.

The phosphor 98 is excited by the laser beam N1, and emits fluorescence FL1 having a wavelength band ranging from the green region to the red region. Mixture of the fluorescence FL1 and the laser beam N1 transmitted through the fluorescence 98 produces normal illumination light. Also, the phosphor 98 is excited by the laser beam N2, and emits fluorescence FL2 having a wavelength band ranging from the green region to the red region. The fluorescence FL2 has slightly less intensity than the fluorescence FL1. Mixture of the fluorescence FL2 and the laser beam N2 transmitted through the phosphor 98 produces special illumination light. The type of the phosphor 98 is not specifically limited, as long as the phosphor is excited by blue excitation light and emits fluorescence having a wavelength band ranging from the green region to the red region. For example, microwhite (trademark) is available.

Figure 33A:
FIG. 33A is an explanatory view of an emission pattern in the normal mode according to the fourth embodiment.
Figure 33B:
FIG. 33B is an explanatory view of an emission pattern in the special mode according to the fourth embodiment.

In the special mode, the source controller 102 turns on only the laser beam source LD1, so the normal illumination light is applied to the internal body portion, as shown in FIG. 33A. In the special mode, on the other hand, the source controller 102 alternately turns on and off the laser beam sources LD1 and LD2, so the normal illumination light and the special illumination light is applied alternately, as shown in FIG. 33B. The normal and special illumination light enters the light guide 43 through the condenser lens 38 and the rod integrator 39.

Figures 34A, 34B:
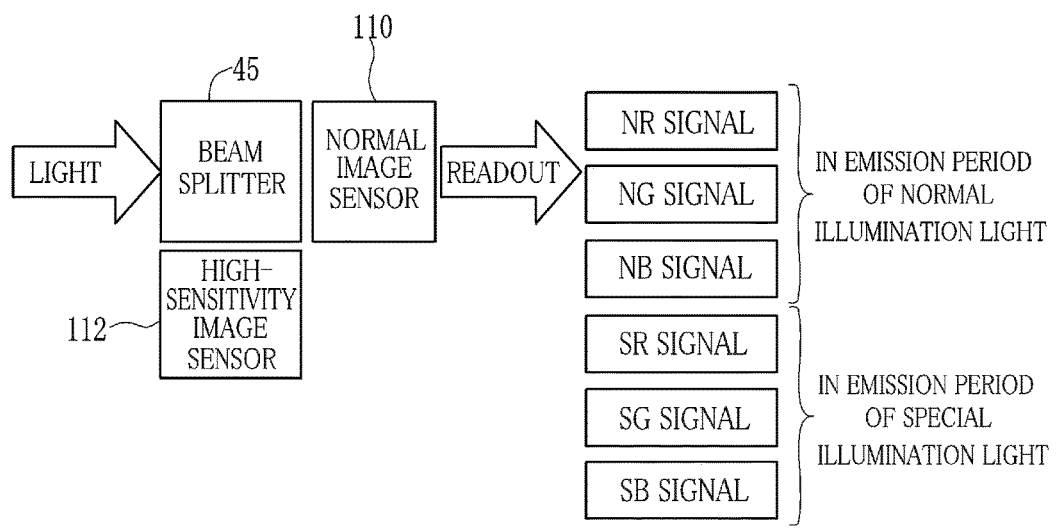
FIG. 34A is a timing chart showing the imaging and readout timing in a case where the light amount of the reflected special light is not judged to be low in the fourth embodiment.
FIG. 34B is an explanatory view of output of the normal signals and the special signals in a case where the light amount is not judged to be low.

The operation of the normal imaging unit 130 and the high-sensitivity imaging unit 131 with the use of the light source device 100 will be hereinafter described. As in the case of the first embodiment, when the reflected light amount of the special illumination light is not low, as shown in FIG. 34A, only the normal image sensor 110 is used. The normal image sensor 110 captures images of the internal body portion irradiated with the normal illumination light and the special illumination light. The normal image sensor 110 performs imaging operation and readout operation of an image signal in each emission period of the normal and special illumination light. Although it is not illustrated in FIG. 34A, in a period between the emission period of the normal illumination light and the emission period of the special illumination light, the electronic shutter is actuated to discharge (reset) electric charge accumulated in the normal image sensor 110. Thus, as shown in FIG. 34B, the normal image sensor 110 outputs NR, NG, and NB signals in the emission period of the normal illumination light, and SR, SG, and SB signals in the emission period of the special illumination light.

When the reflected light amount of the special illumination light is low, as shown in FIG. 35A, not only the normal image sensor 110 but also the high-sensitivity image sensor 112 is used. While the normal image sensor 110 captures the images under irradiation with the normal illumination light, the high-sensitivity image sensor 112 captures the images under irradiation with the special illumination light. The normal image sensor 110 performs the imaging operation and the readout operation in the emission period of the normal illumination light. The high-sensitivity image sensor 112 performs the imaging operation and the readout operation in the emission period of the special illumination light. Therefore, as shown in FIG. 35B, the normal image sensor 110 outputs the NR, NG, and NB signals, and the high-sensitivity image sensor 112 outputs the SR, SG, and SB signals.

Note that, the normal and special illumination light is produced by mixture of the fluorescence and the blue laser beam in the light source device 100. However, the normal and special illumination light may be produced by mixture of white light from a xenon lamp or the like and a laser beam, or mixture of white light and LED light.

In the above embodiments, the SB light having a wavelength of 473 nm is used to produce the special image, but illumination light having another wavelength may be used instead. For example, in the case of connecting an AFI endoscope, which is provided with the high-sensitivity image sensor having an excitation light barrier filter, to the processor device 12 and the light source device 13, it is preferable to use light that is in a transmission wavelength band (for example, 500 to 630 nm) of the barrier filter and has a wavelength (for example, 560±10 nm) at which the absorption coefficient is different between oxyhemoglobin and deoxyhemoglobin.

In the above embodiments, the oxygen saturation level independent from the blood volume is calculated using the SB signal having a narrow band component of 473 nm, the SG signal having a green broad band component, and the SR signal having a red broad band component. However, the oxygen saturation level independent from the depth of the blood vessel may be calculated using a first SB signal having a narrow band component of 445 nm, a second SB signal having a narrow band component of 473 nm, and a third SB signal having a narrow band component of 405 nm. In such a case, the SG filter 42g provided in the outer radial portion 37 of the rotary filter 31 is replaced with a filter transmitting narrow band light of 445±10 nm, and the SR filter 42r is replaced with a filter transmitting narrow band light of 405±10 nm.

Figure 36:
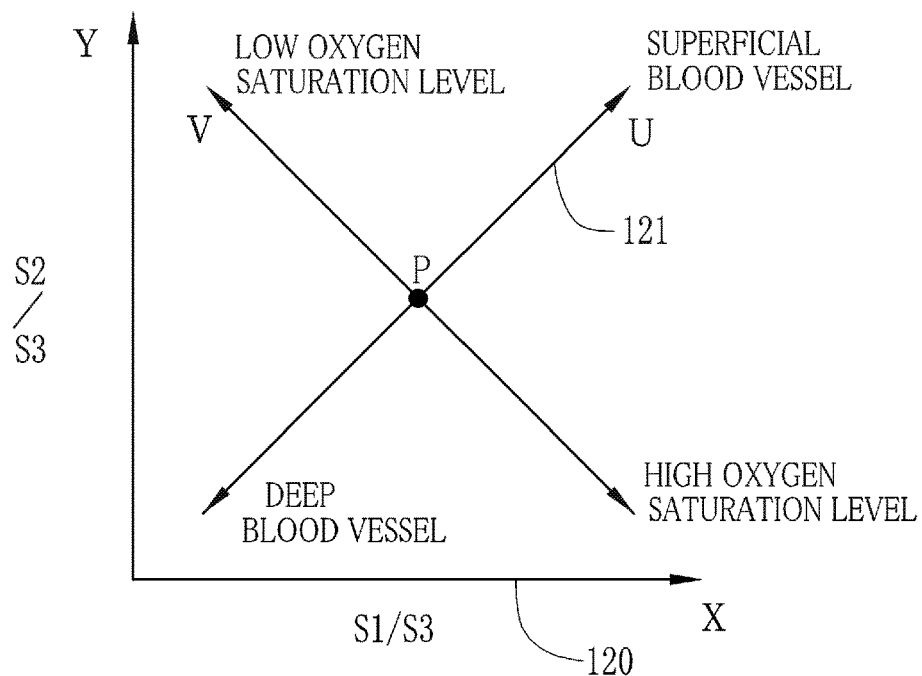
FIG. 36 is a graph showing the correlation among intensity ratios S1/S3 and S2/S3, the depth of a blood vessel, and the oxygen saturation level.

To calculate the oxygen saturation level that is independent from the depth of the blood vessel, the correlation between the depth of the blood vessel and the oxygen saturation level, as shown in FIG. 36, is used. In FIG. 36, a luminance coordinate system 120 is an XY coordinate system having two axes of X and Y. A first intensity ratio S1/S3 between the first and third SB signals is assigned to the X axis. A second intensity ratio S2/S3 between the second and third SB signals is assigned to the Y axis. A blood information coordinate system 121 provided on the luminance coordinate system 120 is a UV coordinate system having two axes of U and V. The depth D of the blood vessel is assigned to the U axis. The oxygen saturation level StO2 is assigned to the V axis.

Since the depth of the blood vessel increases with increase in the first and second intensity ratios S1/S3 and S2/S3, the U axis has a positive gradient to the luminance coordinate system 120. With respect to the U axis, an upper right direction indicates that the blood vessel is superficial, while a lower left direction indicates that the blood vessel is deep. On the other hand, since the oxygen saturation level decreases with increase in the first and second intensity ratios S1/S3 and S2/S3, the V axis has a negative gradient to the luminance coordinate system 120. With respect to the V axis, an upper left direction indicates that the oxygen saturation level StO2 is low, while a lower right direction indicates that the oxygen saturation level StO2 is high. In the blood information coordinate system 121, the U and V axes intersect with each other at right angles at an intersection point P.

Figure 37:
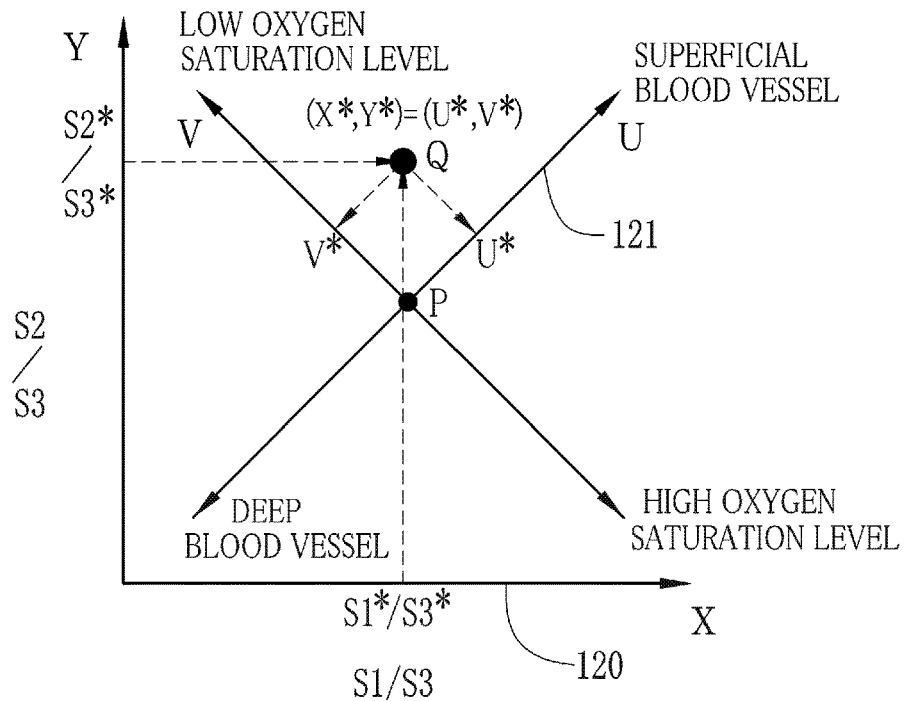
FIG. 37 is a graph for explaining a method for calculating the oxygen saturation level using the correlation of FIG. 36.

To actually calculate the oxygen saturation level, the first intensity ratio S1*/S3* between the first and third SB signals obtained by imaging the body portion, and the second intensity ratio S2*/S3* between the second and third SB signals are calculated. Then, as shown in FIG. 37, coordinates Q (X*, Y*) corresponding to the first and second intensity ratios S1*/S3* and S2*/S3* are plotted on the luminance coordinate system 120. The coordinates Q are projected to each of the V axis representing the oxygen saturation level and the U axis representing the depth of the blood vessel, so the coordinates Q (U*, V*) are determined. Accordingly, "U*" being blood vessel depth information and "V*" being oxygen saturation level information of one pixel are obtained. Such a process is performed in order to obtain the blood vessel depth information and the oxygen saturation level information of all the pixels in a screen. The special image is produced based on the obtained oxygen saturation level information.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
   a light source for applying special illumination light to a body portion, said special illumination light having a wavelength at which oxyhemoglobin and deoxyhemoglobin have different absorption coefficients;
   an imaging device having a normal image sensor and a high-sensitivity image sensor whose sensitivity is higher than that of said normal image sensor, for imaging reflected light of said special illumination light from said body portion;
   a processor configured for:
   measuring a reflected light amount of said special illumination light from said body portion;
   choosing which one of said normal and high-sensitivity image sensors to use for imaging said reflected light of said special illumination light from said body portion in accordance with said measured reflected light amount of said special illumination light; and
   producing a special image depicting an oxygen saturation level of blood based on said signal obtained by imaging said reflected light of said special illumination light from said body portion with use of selected one of said normal and high-sensitivity image sensors
   wherein
   said processor measures said reflected light amount of said special illumination light by using a pixel value outputted from one of said normal and high-sensitivity image sensors, and said processor chooses which one of said normal and high-sensitivity image sensors to use for imaging said reflected light of said special illumination light from said body portion based on said reflected light amount;
   when said normal image sensor is used, said processor stops using said normal image sensor and starts using said high-sensitivity image sensor for imaging said reflected light of said special illumination light from said body portion, if said pixel value corresponding to said reflected light amount is less than a first sensor selection threshold value; and
   when said high-sensitivity image sensor is used, said processor stops using said high-sensitivity image sensor and starts using said normal image sensor for imaging said reflected light of said special illumination light from said body portion, if said pixel value corresponding to said reflected light amount is more than a second sensor selection threshold value, wherein
   said second sensor selection threshold value is larger than said first sensor selection threshold value.

2. The endoscope system according to claim 1, wherein said lighting section sequentially applies to said body portion said special illumination light and normal illumination light having a broader wavelength band than that of said special illumination light, said normal illumination light being used for producing a normal image;
   when said reflected light amount of said special illumination light is low, said imaging control section controls said normal and high-sensitivity image sensors such that said normal image sensor captures said image under irradiation with said normal illumination light and said high-sensitivity image sensor captures said image under irradiation with said special illumination light; and
   when said reflected light amount of said special illumination light is not low, said imaging control section controls said normal and high-sensitivity image sensors such that said normal image sensor captures said image under irradiation with said normal illumination light and said special illumination light.

3. The endoscope system according to claim 1, wherein said normal illumination light includes red light, green light, and blue light;
   said special illumination light includes at least blue narrow band light having a wavelength at which oxyhemoglobin and deoxyhemoglobin have different absorption coefficients; and
   said lighting section selectively emits said red light, said green light, said blue light, and said blue narrow band light.

4. The endoscope system according to claim 1, wherein said normal illumination light is first emission light including first blue narrow band light and fluorescence obtained by wavelength conversion of said first blue narrow band light by a wavelength conversion element;

said special illumination light is second emission light including second blue narrow band light and fluorescence obtained by wavelength conversion of said second blue narrow band light by said wavelength conversion element; and said lighting section selectively emits said first and second emission light.

5. The endoscope system according to claim 1, wherein sensitivity of said high-sensitivity image sensor is 2 to 200 times that of said normal image sensor.

6. The endoscope system according to claim 2, wherein when said reflected light amount of said special illumination light is low, said normal image sensor captures said image under irradiation with said normal illumination light and outputs a color normal signal, and said high-sensitivity image sensor captures said image under irradiation with said special illumination light and outputs a special signal; and said special image processing section produces said special image based on said special signal and a specific color signal of said color normal signal.

7. The endoscope system according to claim 6, wherein when said reflected light amount of said special illumination light is not low, said normal image sensor captures said image under irradiation with said normal illumination light and outputs said color normal signal, and captures said image under irradiation with said special illumination light and outputs said special signal; and said special image processing section produces said special image based on said special signal and said specific color signal of said color normal signal.

8. The endoscope system according to claim 1, further comprising:

a beam splitter for splitting said special illumination light reflected from said body portion into two beams, one of said two beams being incident upon said normal image sensor, the other of said two beams being incident upon said high-sensitivity image sensor, wherein when a first optical path between said beam splitter and said normal image sensor is not equivalent with a second optical path between said beam splitter and said high-sensitivity image sensor, an effective area is defined in each of said normal and high-sensitivity image sensors in such a position as to correspond to an overlapping area in which object images obtained by said normal and high-sensitivity image sensors overlap each other.

9. A processor device of an endoscope system, said endoscope system including a light source for applying to a body portion special illumination light having a wavelength at which oxyhemoglobin and deoxyhemoglobin have different absorption coefficients, and an imaging device having a normal image sensor and a high-sensitivity image sensor whose sensitivity is higher than that of said normal image sensor, for imaging reflected light of said special illumination light from said body portion, said processor device comprising:

measuring a reflected light amount of said special illumination light from said body portion;

choosing which one of said normal and high-sensitivity image sensors to use for imaging said reflected light of said special illumination light from said body portion in accordance with said measured reflected light amount of said special illumination light; and producing a special image depicting an oxygen saturation level of blood based on said signal obtained by imaging said reflected light of said special illumination light from said body portion with use of selected one of said normal and high-sensitivity image sensors wherein said processor measures said reflected light amount of said special illumination light by using a pixel value outputted from one of said normal and high-sensitivity image sensors, and said processor chooses which one of said normal and high-sensitivity image sensors to use for imaging said reflected light of said special illumination light from said body portion based on said reflected light amount;

when said normal image sensor is used, said processor stops using said normal image sensor and starts using said high-sensitivity image sensor for imaging said reflected light of said special illumination light from said body portion, if said pixel value corresponding to said reflected light amount is less than a first sensor selection threshold value; and when said high-sensitivity image sensor is used, said processor stops using said high-sensitivity image sensor and starts using said normal image sensor for imaging said reflected light of said special illumination light from said body portion, if said pixel value corresponding to said reflected light amount is more than a second sensor selection threshold value, wherein said second sensor selection threshold value is larger than said first sensor selection threshold value.

10. A method for controlling an endoscope system, said endoscope system including a light source for applying to a body portion special illumination light having a wavelength at which oxyhemoglobin and deoxyhemoglobin have different absorption coefficients, and an imaging device having a normal image sensor and a high-sensitivity image sensor whose sensitivity is higher than that of said normal image sensor, for imaging reflected light of said special illumination light from said body portion, said method comprising the steps of:

applying said special illumination light to said body portion;

guiding said special illumination light reflected from said body portion to said imaging section;

measuring a reflected light amount of said special illumination light from said body portion;

choosing which one of said normal and high-sensitivity image sensors to use for imaging said reflected light of said special illumination light from said body portion in accordance with said measured reflected light amount of said special illumination light;

operating said normal and high-sensitivity image sensors in said changed operating conditions, and imaging said body portion under irradiation with said special illumination light;

producing a special image depicting an oxygen saturation level of blood based on an image signal obtained by imaging said reflected light of said special illumination light from said body portion with use of selected one of said normal and high-sensitivity image sensors;

measuring said reflected light amount of said special illumination light by using a pixel value outputted from one of said normal and high-sensitivity image sensors, and choosing which one of said normal and high-sensitivity image sensors to use for imaging said reflected light of said special illumination light from said body portion based on said reflected light amount; wherein when said normal image sensor is used, said normal image sensor is not used and said high-sensitivity image sensor is used for imaging said reflected light of said special illumination light from said body portion, if said pixel value corresponding to said reflected light amount is less than a first sensor selection threshold value; and when said high-sensitivity image sensor is used, said high-sensitivity image sensor is not used and said normal image sensor is used for imaging said reflected light of said special illumination light from said body portion, if said pixel value corresponding to said reflected light amount is more than a second sensor selection threshold value, wherein said second sensor selection threshold value is larger than said first sensor selection threshold value.

11. The endoscope system according to claim 3, wherein the normal illumination light and the special illumination light are generated by filtering broadband light with a wavelength filter.

* * * * *